US010655149B2

(12) United States Patent
Dechman et al.

(10) Patent No.: US 10,655,149 B2
(45) Date of Patent: May 19, 2020

(54) PRETREATMENT OF LIGNOCELLULOSIC BIOMASS WITH SULFUR DIOXIDE AND/OR SULFUROUS ACID

(71) Applicant: Iogen Corporation, Ottawa (CA)

(72) Inventors: John Dechman, Ottawa (CA); Brian Foody, Ottawa (CA)

(73) Assignee: Iogen Corporation, Ottawa (CA)

( * ) Notice: Subject to any disclaimer, the term of this patent is extended or adjusted under 35 U.S.C. 154(b) by 149 days.

(21) Appl. No.: 16/076,457

(22) PCT Filed: Sep. 16, 2016

(86) PCT No.: PCT/CA2016/051089
§ 371 (c)(1),
(2) Date: Aug. 8, 2018

(87) PCT Pub. No.: WO2017/136915
PCT Pub. Date: Aug. 17, 2017

(65) Prior Publication Data
US 2019/0194697 A1 Jun. 27, 2019

Related U.S. Application Data

(60) Provisional application No. 62/293,481, filed on Feb. 10, 2016.

(51) Int. Cl.
| | |
|---|---|
| *C12P 7/10* | (2006.01) |
| *C12P 19/02* | (2006.01) |
| *C12P 19/14* | (2006.01) |
| *C10L 1/02* | (2006.01) |
| *C13K 1/02* | (2006.01) |

(52) U.S. Cl.
CPC ............ *C12P 7/10* (2013.01); *C10L 1/02* (2013.01); *C12P 19/02* (2013.01); *C12P 19/14* (2013.01); *C13K 1/02* (2013.01); *C12P 2201/00* (2013.01); *C12P 2203/00* (2013.01); *C12Y 302/01004* (2013.01); *Y02E 50/16* (2013.01)

(58) Field of Classification Search
None
See application file for complete search history.

(56) References Cited

U.S. PATENT DOCUMENTS

| | | | |
|---|---|---|---|
| 2,418,167 A | 4/1947 | Du Bois | |
| 4,461,648 A | 7/1984 | Foody | |
| 5,424,417 A | 6/1995 | Torget et al. | |
| 5,789,210 A | 8/1998 | Ho et al. | |
| 5,866,382 A | 2/1999 | Hallborn et al. | |
| 6,475,768 B1 | 11/2002 | Otero et al. | |
| 6,582,944 B1 | 6/2003 | Hallborn et al. | |
| 7,527,927 B1 | 5/2009 | Ho et al. | |
| 7,527,951 B2 | 5/2009 | Londesborough et al. | |
| 7,622,284 B2 | 11/2009 | Op Den Camp et al. | |
| 8,038,842 B2 | 10/2011 | Retsina et al. | |
| 8,268,125 B2 | 9/2012 | Retsina et al. | |
| 8,409,836 B2 | 4/2013 | Vehmaanpera et al. | |
| 8,709,770 B2 | 4/2014 | Harlick et al. | |
| 8,728,243 B2 | 5/2014 | Van Der Meulen et al. | |
| 8,815,499 B2 | 8/2014 | Alriksson et al. | |
| 8,834,633 B2 | 9/2014 | Van Der Meulen et al. | |
| 8,871,475 B2 | 10/2014 | Alriksson et al. | |
| 9,012,188 B2 | 4/2015 | Van Heiningen et al. | |
| 9,090,915 B2 | 7/2015 | Wang et al. | |
| 9,102,951 B2 | 8/2015 | Griffin et al. | |
| 9,284,382 B2 | 3/2016 | Chen et al. | |
| 9,290,821 B2 | 3/2016 | Blackbourn et al. | |
| 9,574,212 B2 | 2/2017 | Foody et al. | |
| 2007/0254348 A1 | 11/2007 | Retsina et al. | |
| 2009/0118477 A1 | 5/2009 | Hallberg et al. | |
| 2010/0056774 A1 | 3/2010 | Anand et al. | |
| 2010/0279361 A1 | 11/2010 | South et al. | |
| 2011/0300586 A1 | 12/2011 | Liu et al. | |
| 2012/0041186 A1 | 2/2012 | Pschorn et al. | |
| 2013/0071903 A1 | 3/2013 | Rowland et al. | |
| 2014/0053827 A1 | 2/2014 | Macedo Baudel et al. | |
| 2014/0109897 A1 | 4/2014 | Chen et al. | |
| 2014/0154746 A1 | 6/2014 | Jonsson et al. | |

(Continued)

FOREIGN PATENT DOCUMENTS

| | | |
|---|---|---|
| EP | 0 450 430 B1 | 10/1991 |
| EP | 0 715 657 B1 | 6/1996 |

(Continued)

OTHER PUBLICATIONS

Behera et al., "Importance of chemical pretreatment for bioconversion of lignocellulosic biomass" 2014, Renewable and Sustainable Energy Reviews, pp. 91-106, vol. 36.

Bensah, E. and Mensah, M., "Chemical Pretreatment Methods for the Production of Cellulosic Ethanol: Technologies and Innovations," International Journal of Chemical Engineering, 2013, pp. 1-21, vol. 2013.

Bhalla et al., "Improved lignocellulose conversion to biofuels with thermophilic bacteria and thermostable enzymes," Bioresource Technology, 2013, pp. 751-759, vol. 128.

Boussaid et al., "Fermentability of the Hemicellulose-Derived Sugars from Steam-Exploded Softwood (Douglas Fir)," Biotechnology and Bioengineering, 1999, pp. 284-289, vol. 64, No. 3.

(Continued)

*Primary Examiner* — Thane Underdahl
(74) *Attorney, Agent, or Firm* — Knobbe Martens Olson & Bear LLP

(57) ABSTRACT

A process for hydrolyzing lignocellulosic biomass includes feeding lignocellulosic biomass into a pretreatment reactor, wherein the pretreatment reactor has a headspace charged with sulfur dioxide previously used in the pretreatment of lignocellulosic biomass. In addition, acid comprising sulfur dioxide and/or sulfurous acid is fed into the pretreatment reactor (e.g., with the lignocellulosic biomass, separate from the lignocellulosic biomass, or a combination thereof) and the lignocellulosic biomass is heated. As the pretreated lignocellulosic biomass is discharged from the pretreatment reactor, at least a portion of the sulfur dioxide used in the pretreatment is retained in the headspace.

21 Claims, 5 Drawing Sheets

(56) References Cited

U.S. PATENT DOCUMENTS

| | | | |
|---|---|---|---|
| 2014/0163210 A1 | 6/2014 | Retsina et al. | |
| 2014/0178944 A1 | 6/2014 | Parekh et al. | |
| 2014/0182582 A1 | 7/2014 | Retsina et al. | |
| 2014/0186899 A1 | 7/2014 | Retsina et al. | |
| 2014/0186903 A1 | 7/2014 | Retsina et al. | |
| 2015/0259709 A1 | 9/2015 | Retsina et al. | |

FOREIGN PATENT DOCUMENTS

| | | | |
|---|---|---|---|
| WO | WO 2002/070753 A3 | 9/2002 | |
| WO | WO 2006/026863 A1 | 3/2006 | |
| WO | WO 2006/034590 A1 | 4/2006 | |
| WO | WO 2006/034591 A1 | 4/2006 | |
| WO | WO 2006/128304 A1 | 12/2006 | |
| WO | WO 2008/041840 A1 | 4/2008 | |
| WO | WO 2009/026722 A1 | 3/2009 | |
| WO | WO 2010/022511 A1 | 3/2010 | |
| WO | WO 2010/046532 A1 | 4/2010 | |
| WO | WO 2013/113579 A1 | 8/2013 | |
| WO | WO 2014/106222 A2 | 7/2014 | |
| WO | WO 2016/094594 A1 | 6/2016 | |
| WO | WO 2016/145527 A1 | 9/2016 | |
| WO | WO 2016/145528 A1 | 9/2016 | |
| WO | WO 2016/145529 A1 | 9/2016 | |
| WO | WO 2016/145531 A1 | 9/2016 | |
| WO | WO 2017/136915 A1 | 8/2017 | |

OTHER PUBLICATIONS

Brownell, H. and Saddler, J., "Steam Pretreatment of Lignocellulosic Material for Enhanced Enzymatic Hydrolysis," Biotechnology and Bioengineering, 1987, pp. 228-235, vol. 29.
Bura et al., "Influence of Xylan on the Enzymatic Hydrolysis of Steam-Pretreated Corn Stover and Hybrid Poplar," Biotechnol Prog, 2009, pp. 315-322, vol. 25, No. 2.
Bura et al., "Moving towards commercialization of lignocellulosic biomass to fuels to chemicals. How to deal with heterogeneous biomass?" University of Washington Biofuels and Bioproducts Laboratory, 2012.
Bura et al., "Optimization of SO2-Catalyzed Steam Pretreatment of Corn Fiber for Ethanol Production", Applied Biochemistry and Biotechnology, 2003, vol. 105-108, pp. 319-335.
Bura et al., "SO2-Catalyzed Steam Explosion of Corn Fiber for Ethanol Production," Applied Biochemistry and Biotechnology, 2002, pp. 59-72, vols. 98-100.
Carrasco et al., "SO2-catalysed steam pretreatment of quinoa stalks," J Chem Technol Biotechnol, 2015, pp. 64-71, vol. 90.
Carrasco et al., "SO2-catalyzed steam pretreatment and fermentation of enzymatically hydrolyzed sugarcane bagasse," Enzyme and Microbial Technology, 2010, pp. 64-73, vol. 46.
Carrasco, "Arabinosylated phenolics obtained from SO2-steam-pretreated sugarcane bagasse," Journal of Chemical Technology and Biotechnology, 2012, pp. 1723-1726, vol. 87.
Chacha et al., "Steam Pretreatment of Pine (Pinus patula) Wood Residue for the Production of Reducing Sugars," Cellulose Chemistry and Technology, 2011, pp. 495-501, vol. 45 (7-8).
Chandra et al., "Enhancing Hemicellulose Recovery and the Enzymatic Hydrolysis of Cellulose by Adding Lignosulfonates during the Two-Stage Steam Pretreatment of Poplar," ACS Sustainable Chem Eng, 2015, pp. 986-991, vol. 3.
Cheng et al., "High titer and yield ethanol production from undetoxified whole slurry of Douglas-fir forest residue using pH profiling in SPORL," Biotechnology for Biofuels, 2015, pp. 1-10, vol. 8:22.
Clark et al., "Steam Explosion of the Softwood Pinus Radiata with Sulphur Dioxide Addition. II. Process Characterisation," Journal of Wood Chemistry and Technology, 1989, pp. 135-166, vol. 9:2.
Clark et al., "Steam Explosion of the Softwood Pinus Radiata with Sulphur Dioxide Addition. I. Process Optimization," Journal of Wood Chemistry and Technology, 1987, pp. 373-403, vol. 7:3.

Corrales et al., "Structural evaluation of sugar cane bagasse steam pretreated in the presence of CO2 and SO2," Biotechnology for Biofuels, 2012, pp. 1-8, vol. 5:36.
De Bari et al., "SO2-Catalyzed Steam Fractionation of Aspen Chips for Bioethanol Production: Optimization of the Catalyst Impregnation," Ind. Eng. Chem. Res, 2007, pp. 7711-7720, vol. 46.
Dekker, R.F.H. et al., "Enzymic Saccharification of Sugarcane Bagasse Pretreated by Autohydrolysis-Steam Explosion," Biotechnology and Bioengineering, 1983, pp. 3027-3048, vol. XXV.
Dekker, Robert F. H., "The Utilization of Autohydrolysis-Exploded Hardwood (Eucalyptus Regnans) and Softwood (Pinus Radiata) Sawdust for the Production of Cellulolytic Enzymes and Fermentable Substrates," Biocatalysis, 1987, pp. 63-75, vol. 1.
Ehsanipour, Mandana, "Bioconversion of lignocellulosic hydrolysate to acetic acid using Moorella thermoacetica," a thesis submitted in partial fulfillment of the requirements for the degree of Master of Science at University of Washington, 2015.
Eklund et al., "The Influence of SO2 and H2SO4 Impregnation of Willow Prior to Steam Pretreatment," 1995, Bioresource Engineering, pp. 225-229, vol. 52.
Elander et al., "Summary of findings from the Biomass Refining Consortium for Applied Fundamentals and Innovation (CAFI): corn stover pretreatment," 2009, Cellulose, pp. 649-659, vol. 16.
Ewanick et al., "The effect of biomass moisture content on bioethanol yields from steam pretreated switchgrass and sugarcane bagasse," 2011, Bioresource Technology, pp. 2651-2658, vol. 102.
Fan et al., "Optimization of SO2-catalyzed hydrolysis of corncob for xylose and xylitol production," 2014, J Chem Technol Biotechnol, pp. 1720-1726, vol. 89.
Galbe et al., "A review of the production of ethanol from softwood," 2002, Appl Microbial Biotechnol, pp. 618-628, vol. 59.
Garlock et al., "Comparative material balances around pretreatment technologies for the conversion of switchgrass to soluble sugars," 2011, Bioresource Technology, pp. 11063-11071, vol. 102.
Gregg et al., "A Techno-Economic Assessment of the Pretreatment and Fractionism Steps of a Biomass-to-Ethanol Process," 1996, Applied Biochemistry and Biotechnology, pp. 711-727, vol. 57/58.
Gu et al., "Fermentative High-Titer Ethanol Production from Douglas-Fir Forest Residue Without Detoxification Using SPORL: High SO2 Loading at Low Temperature," 2016, Industrial Biotechnology, pp. 168-175, vol. 12, No. 3.
Harris et al., "Stimulation of Lignocellulosic Biomass Hydrolysis by Proteins of Glycoside Hydrolase Family 61: Structure and Function of a Large, Enigmatic Family," 2010, Biochemistry, pp. 3305-3316, vol. 49.
Hodge et al., "Soluble and insoluble solids contributions to high-solids enzymatic hydrolysis of lignocellulose," 2008, Bioresource Technology, pp. 8940-8948, vol. 99.
Kumar et al., "Access of Cellulase to Cellulose and Lignin for Poplar Solids Produced by Leading Pretreatment Technologies," 2009, Biotechnol. Prog., pp. 807-819, vol. 25, No. 3.
Lan et al., "High titer ethanol production from SPORL-pretreated lodgepole pine by simultaneous enzymatic saccharification and combined fermentation," 2013, Bioresource Technology, pp. 291-297, vol. 127.
Leu et al., "Substrate-Related Factors Affecting Enzymatic Saccharification of Lignocelluloses; Our Recent Understanding," 2013, Bioenerg. Res., pp. 405-415, vol. 6.
Liu et al., "Effect of Sulfite Pretreatment to Overcome the Recalcitrance of Lignin (SPORL) on Enzymatic Saccharification of Corn Stalk," 2011, Bioresouces, 5001-5011, vol. 6(4).
Mackie et al., "Effect of Sulphur Dioxide and Sulphuric Acid on Steam Explosion of Aspenwood," 1985, Journal of Wood Chemistry and Technology, pp. 405-425, vol. 5(3).
Mamers et al., "Explosion pretreatment of Pinus radiata woodchips for the production of fermentation substrates," 1984, Apita, pp. 644-649, vol. 37, No. 8.
Martin et al., "Comparison of the Fermentability of Enzymatic Hydrolyzates of Sugarcane Bagasse Pretreated by Steam Explosion Using Different Impregnating Agents," 2002, Applied Biochemistry and Biotechnology, pp. 699-716, vol. 98-100.

(56) References Cited

OTHER PUBLICATIONS

Monavari et al., "Improved One-Step Steam Pretreatment if SO2-Impregnated Softwood with Time-Dependant Temperature Profile for Ethanol Production," 2010, Biotechnol. Prog., pp. 1054-1060, vol. 26, No. 4.
Nguyen et al., "Dilute Acid Pretreatment of Softwoods," 1998, Applied Biochemistry and Biotechnology, pp. 77-89, vol. 70-72.
Nguyen et al., "Two-Stage Dilute Acid Pretreatment of Softwoods," 2000, Applied Biochemistry and Biotechnology, 561-576, vol. 84-86.
Ohgren et al., "Optimization of Steam Pretreatment of SO2-Impregnated Corn Stover for Fuel Ethanol Production," 2005, Applied Biochemistry and Biotechnology, pp. 1055-1067, vol. 121-124.
Pedersen et al., "Low temperature lignocellulose pretreatment: effects and interactions of pretreatment pH are critical for maximizing enzymatic monosaccharide yields from wheat straw," 2011, Biotechnology for Biofuels, pp. 1-10, vol. 4:11.
Rakkolainen et al., "SO2-Ethanol-Water Fractionation of Forest Biomass and Implications for Biofuel Production by Abe Fermentation," 2010, Cellulose Chem. Technol., pp. 139-145, vol. 44.
Ramos et al., "Characterization of Residual Lignin after SO2-Catalyzed Steam Explosion and Enzymatic Hydrolysis of Eucalyptus viminalis Wood Chips," 1999, J. Agric. Food Chem., pp. 2295-2302, vol. 47.
Ramos et al., "Comparison of Steam Pretreatment of Eucalyptus, Aspen, and Spruce Wood Chips and their Enzymatic Hydrolysis," 1992, Applied Biochemistry and Biotechnology, pp. 37-48, vol. 34/35.
Ramos et al., "Effect of enzymatic hydrolysis on the morphology and fine structure of pretreated cellulosic residues," 1993, Enzyme Microb. Technol., pp. 821-831, vol. 15.
Sassner et al., "Steam Pretreatment of Salix with and without SO2 Impregnation for Production of Bioethanol," 2005, Applied Biochemistry and Biotechnology, pp. 1101-1117, vol. 121-124.
Schell et al., "A Technical and Economic Analysis of Acid-Catalyzed Steam Explosion and Dilute Sulfuric Acid Pretreatments Using Wheat Straw or Aspen Wood Chips," 1991, Applied Biochemistry and Biotechnology, pp. 87-97, vol. 28/29.
Schell et al., "Pretreatment of Softwood by Acid-Catalyzed Steam Explosion Followed by Alkali Extraction," 1998, Applied Biochemistry and Biotechnology, pp. 17-24, vol. 70-72.
Schwald et al., "Assessment of Pretreatment Conditions to Obtain Fast Complete Hydrolysis on High Substrate Concentrations," 1989, Applied Biochemistry and Biotechnology, pp. 29-44, vol. 20/21.
Sendelius, "Steam Pretreatment Optimisation for Sugarcane Bagasse in Bioethanol Production," 2005, Master of Science Thesis, Lund University, Sweden.
Shevchenko et al., "Optimization of monosaccharide recovery by post-hydrolysis of the water-soluble hemicellulose component after steam explosion of softwood chips," 2000, Bioresource Technology, pp. 207-211, vol. 72.
Shevchenko et al., "The Nature of Lignin from Steam Explosion/Enzymatic Hydrolysis of Softwood," 1999, Applied Biochemistry and Biotechnology, pp. 867-876, vol. 77-79.
Shi et al., "Sugar yields from dilute sulfuric acid and sulfur dioxide pretreatments and subsequent enzymatic hydrolysis of switchgrass," 2011, Bioresource Technology, pp. 8930-8938, vol. 102.
Shuai et al., "Comparative study of SPORL and dilute-acid pretreatments of spruce for cellulosic ethanol production," 2010, Bioresource Technology, pp. 3106-3114, vol. 101.
Sipos et al., "Steam pretreatment of dry and ensiled industrial hemp for ethanol production," 2010, Biomass and Bioenergy, pp. 1-11.
Sluiter et al., "Determination of Structural Carbohydrates and Lignin in Biomass," NREL Technical Report 2012.
Soderstrom et al., "Effect of Washing on Yield in One- and Two-Step Steam Pretreatment of Softwood for Production of Ethanol," 2004, Biotechnol. Prog., pp. 744-749, vol. 20.
Soderstrom et al., "Separate versus Simultaneous Saccharification and Fermentation of Two-Step Steam Pretreated Softwood for Ethanol Production," 2005, Journal of Wood Chemistry, pp. 187-202, vol. 25.
Soderstrom et al., "Two-Step Steam Pretreatment of Softwood with SO2 Impregnation for Ethanol Production," 2002, Applied Biochemistry and Biotechnology, pp. 5-21, vol. 98-100.
Stelte, Wolfgang, "Steam explosion for biomass pre-treatment," Danish Technological Institute (2013), pp. 1-15.
Stenberg et al, "Optimisation of Steam Pretreatment of SO2-Impregnated Mixed Softwoods for Ethanol Production," 1998, J. Chem. Technol. Biotechnol, pp. 299-308, vol. 71.
Szengyel et al., "Cellulase Production of Trichoderma reesei Rut C 30 Using Steam-Pretreated Spruce," 2000, Applied Biochemistry and Biotechnology, pp. 679-691, vol. 84-86.
Tao et al.,"Process and technoeconomic analysis of leading pretreatment technologies for lignocellulosic ethanol production using switchgrass," 2011, Bioresource Technology, pp. 11105-11114, vol. 102.
Tengborg et al., "Comparison of SO2 and H2SO4 Impregnation of Softwood Prior to Steam Pretreatment on Ethanol Production," 1998, Applied Biochemistry and Biotechnology, pp. 3-15, vol. 70-72.
Tengborg et al., "Reduced inhibition of enzymatic hydrolysis of steam-pretreated softwood," 2001, Enzyme and Microbial Technology, pp. 835-844, vol. 28.
Tian et al., "Comparisons of SPORL and Dilute Acid Pretreatments for Sugar and Ethanol Productions from Aspen," 2011, Biotechnol. Prog. pp. 419-427, vol. 27, No. 2.
Tian et al., "Robust cellulosic ethanol production from SPORL-pretreated lodgepole pine using an adapted strain *Saccharomyces cerevisiae* without detoxification," 2010, Bioresource Technology, pp. 8678-8685, vol. 101.
Trajano et al., "Fundamentals of Biomass Pretreatment at Low pH," 2013, Aqueous Pretreatment of Plant Biomass for Biological and Chemical Conversion to Fuels and Chemicals, pp. 103-128.
Vera et al., "Synergistic effects of mixing hybrid poplar and wheat straw biomass for bioconversion processes," 2015, Biotechnol Biofuels, pp. 1-10, vol. 8:226.
Von Sivers et al., "A Techno-Economical Comparison of Three Processes for the Production of Ethanol from Pine," 1995, Bioresource Technology, pp. 43-52, vol. 51.
Wang et al., "Ethanol production from poplar wood through enzymatic saccharification and fermentation by dilute acid and SPORL pretreatments," 2012, Fuel, pp. 606-614, vol. 95.
Wang et al., "Lignosulfonate and elevated pH can enhance enzymatic saccharification of lignocelluloses," 2013, Biotechnology for Biofuels, pp. 1-10, vol. 6:9.
Wang et al., "Sulfite Pretreatment to Overcome Recalcitrance of Lignocellulose (SPORL) for Robust Enzymatic Saccharification of Hardwoods," 2009, Biotechnol. Prog., pp. 1086-1093, vol. 25, No. 4.
Wayman et al., "Hydrolysis of Biomass by Sulphur Dioxide," 1984, Biomass, pp. 183-191, vol. 6.
Wayman et al., "SO2 Catalysed Prehydrolysis of Coniferous Wood for Ethanol Production," 1986, Biotechnology Letters, pp. 749-752, vol. 8, No. 10.
Wiman et al., "Cellulose accessibility determines the rate of enzymatic hydrolysis of steam-pretreated spruce," 2012, Bioresource Technology, pp. 208-215, vol. 126.
Wolfinger et al., "Modeling of the Acid Sulfite Pulping Process.—Problem Definition and Theoretical Approach for a Solution with the Main Focus on the Recovery of Cooking Chemicals," 2004, Lenzinger Berichte, pp. 35-45, vol. 83.
Wooley, Bob, "Production of 1,000 Gallons of BioJet," 2015, Presentation from 2015 Annual Meeting of Northwest Advanced Renewables Alliance (NARA).
Wyman et al., "Comparative data on effects of leading pretreatments and enzyme loadings and formulations on sugar yields from different switchgrass sources," 2011, Bioresource Technology, 11052-11062, vol. 102.

(56) References Cited

OTHER PUBLICATIONS

Wyman et al., "Comparative Sugar Recovery and Fermentation Data Following Pretreatment of Poplar Wood by Leading Technologies," 2009, Biotechnol. Prog., pp. 333-339, vol. 25, No. 2.

Zhang et al., "Sulfite (SPORL) pretreatment of switchgrass for enzymatic saccharification," 2013, Bioresource Technology, pp. 127-134, vol. 129.

Zhou et al., "Bioconversion of Beetle-Killed Lodgepole Pine Using SPORL: Process Scale-Up Design, Lignin Coproduct, and High Solids Fermentation without Detoxification," 2013, Industrial & Engineering Chemistry Research, pp. A-I.

Zhu et al., "Ethanol production from SPORL-pretreated lodgepole pine: preliminary evaluation of mass balance and process energy efficiency," 2010, Appl Microbiol Biotechnol, pp. 1355-1365, vol. 86.

Zhu et al., "High Titer Ethanol Production from Forest Residue Using Sulfite Mill Pulping Chemistry," 2015, Presentation at 2015 TAPPI IBBC.

Zhu et al., "High titer ethanol production from simultaneous enzymatic saccharification and fermentation of aspen at high solids: A comparison between SPORL and dilute acid pretreatments," 2011, Bioresource Technology, pp. 8921-8929, vol. 102.

Zhu et al., "On Polydispersity of Plant Biomass Recalcitrance and Its Effects on Pretreatment Optimization for Sugar Production," 2011, Bioenerg. Res., pp. 201-210, vol. 4.

Zhu et al., "Quantitative predictions of bioconversion of aspen by dilute acid and SPORL pretreatments using a unified combined hydrolysis factor (CHF)," 2012, Process Biochemistry, pp. 785-791, vol. 47.

Zhu et al., "Sulfite pretreatment (SPORL) for robust enzymatic saccharification of spruce and red pine," 2009, Bioresource Technology, pp. 2411-2418, vol. 100.

Zhu et al., "Using sulfite chemistry for robust bioconversion of Douglas-fir forest residue to bioethanol at high titer and lignosulfonate: A pilot-scale evaluation," 2015, Bioresource Technology, pp. 390-397, vol. 179.

Zhu et al., "Woody biomass pretreatment for cellulosic ethanol production: Technology and energy consumption evaluation," 2010, Bioresource Technology, pp. 4992-5002, vol. 101.

International Search Report and Written Opinion dated Nov. 9, 2016 for International Application No. PCT/CA2016/051089, filed Sep. 16, 2016.

PRETREATMENT OF LIGNOCELLULOSIC BIOMASS WITH SULFUR DIOXIDE AND/OR SULFUROUS ACID

This application is a national stage application of PCT/CA2016/051089 having an international filing date of Sep. 16, 2016, which claims benefit of U.S. provisional application No. 62/293,481 filed Feb. 10, 2016, each of which is hereby incorporated by reference.

TECHNICAL FIELD

The present disclosure relates generally to a process for pretreating and hydrolyzing lignocellulosic biomass, and in particular, to a process comprising pretreatment of lignocellulosic biomass with sulfur dioxide and/or sulfurous acid.

BACKGROUND

The production of transportation fuels (e.g., ethanol) from biomass continues to attract interest due to the wide availability of biomass, environmental benefits, and because biofuels may be used to displace the use of fossil fuels. For example, ethanol may be blended into gasoline at predetermined concentrations (e.g., 10%).

First generation biofuels, also referred to as conventional biofuels, are made from biomass that contains sugar, starch, or vegetable oil. For example, ethanol may be produced by fermenting sugars that are easily extracted from sugar crops (e.g., sugar cane or sugar beets), or may be produced by fermenting sugars derived from starch-based feedstocks (e.g., corn grain, barley, wheat, potatoes, cassava). In fact, the diversion of farmland or crops for first generation biofuel production has led to much debate about increased food prices and/or decreased food supplies associated therewith. In addition, there are concerns related to the energy and environmental impact of these production processes.

Second generation biofuels, also referred to as advanced biofuels, wherein the biomass contains lignocellulosic material and/or is obtained from agricultural residues or waste (e.g., corn cobs, corn stover (e.g., stocks and leaves), bagasse, wood chips, wood waste), may allay some of these concerns. For example, when bioethanol produced using second generation processes (i.e., also referred to as cellulosic ethanol) is derived from agricultural waste or residue, its production should not affect the food supply. In fact, tremendous effort is currently being expended to advance cellulosic ethanol production processes.

Lignocellulosic biomass typically contains cellulose, hemicellulose and lignin, each of which is present in plant cell walls. Cellulose (e.g., a type of glucan) is an unbranched chain polysaccharide including hexose (C6) sugar monomers (e.g., glucose). Hemicellulose is a branched chain polysaccharide that may include different pentose (C5) sugar monomers (e.g., xylose and arabinose) in addition to glucose. Lignin is a complex organic polymer, which typically includes cross-linked phenol polymers. Although generally insoluble in water at mild conditions, lignin may be soluble in varying degrees in dilute acid or base alkali. The ratio and/or structure of these components may vary depending on the source of the biomass.

The production of ethanol from lignocellulosic biomass most often involves breaking down the cellulose and/or hemicellulose into the constituent sugars, which may then be fermented. Unfortunately, the cellulose, hemicellulose, and/or lignin found in lignocellulosic biomass is typically structured within the plant walls to resist degradation.

Since lignocellulosic biomass is naturally resistant to breakdown into its constituent sugars, a pretreatment step is often used to open up the structure of the material and/or to make it accessible for enzymes used to hydrolyze the cellulosic component. Some examples of pretreatments include dilute acid pretreatment, alkali pretreatment (e.g., lime), ammonia fiber expansion, autohydrolysis (e.g., hot water extraction that does not require the addition of acid or base), steam explosion, organic solvent, and/or wet oxidation.

One type of pretreatment is sulfur dioxide ($SO_2$)-catalyzed steam pretreatment. Sulfur dioxide is a gas, which when dissolved in water, is referred to as sulfurous acid. Sulfur dioxide and/or sulfurous acid may be a suitable catalyst for acid-catalyzed steam pretreatment since it may produce a more digestible substrate and/or may produce less/fewer inhibitors relative to other acid pretreatments, such as dilute sulfuric acid ($H_2SO_4$) catalyzed pretreatments. In addition, sulfur dioxide catalyzed pretreatment may be effective at relatively low temperatures and/or reaction times (e.g., relative to dilute sulfuric acid pretreatments).

Although sulfur dioxide catalyzed pretreatment offers some advantages over dilute sulfuric acid catalyzed pretreatments, the use of sulfur dioxide is often considered expensive and/or is associated with environmental concerns. For example, in a conventional batch pretreatment, the sulfur dioxide and/or sulfurous acid is added to lignocellulosic biomass, pressurized and/or heated (e.g., with steam), and then depressurized and discharged from the reactor. Once the reactor has been emptied it may be loaded with additional lignocellulosic biomass and sulfur dioxide/sulfurous acid. Cost and environmental concerns arise because a significant makeup amount of sulfur dioxide may be required (e.g., or generated if using sulfurous acid) for each sequential batch, which may also need to be recovered.

SUMMARY

The present disclosure describes one or more embodiments of a method and/or system wherein the pretreatment of lignocellulosic biomass is designed to reduce the total amount of sulfur dioxide used and/or that needs to be recovered. For example, in one embodiment, a reactor used for conducting pretreatment (i.e., a pretreatment reactor) is provided with a charge of sulfur dioxide that substantially remains in a headspace of the reactor as the pretreated lignocellulosic biomass within the reactor is discharged. Since at least some of the sulfur dioxide remains within the headspace, it is available to help drive the pretreatment of additional lignocellulosic biomass (e.g., biomass from a different batch and/or biomass upstream of the pretreatment reactor). Accordingly, less sulfur dioxide/sulfurous acid needs to be added to achieve the desired sulfur dioxide concentration within the pretreatment reactor and/or less sulfur dioxide needs to be recovered. Advantageously, process economics may be improved as a result of using less sulfur dioxide and/or sulfurous acid.

One aspect of the present disclosure is directed to a process for hydrolyzing lignocellulosic biomass comprising: a) feeding lignocellulosic biomass and acid into a pretreatment reactor, said acid comprising at least one of sulfur dioxide and sulfurous acid; b) heating said lignocellulosic biomass in the pretreatment reactor for a time and at a temperature sufficient to provide a slurry comprising pretreated lignocellulosic biomass, said slurry adjacent a headspace comprising sulfur dioxide; c) removing said slurry from the pretreatment reactor; d) preventing at least a portion of the sulfur dioxide in the headspace from exiting the pretreatment reactor as the slurry is removed; e) hydrolyzing cellulose in the slurry in the presence of cellulase to produce glucose; and f) contacting additional lignocellulosic biomass with the sulfur dioxide prevented from exiting the pretreatment reactor in step d) under conditions selected to pretreat the additional lignocellulosic biomass.

One aspect of the present disclosure is directed to a process for pretreating lignocellulosic biomass comprising: a) feeding acid and lignocellulosic biomass into a pretreatment reactor, said acid comprising at least one of sulfur dioxide and sulfurous acid, said acid added to the pretreatment reactor with the lignocellulosic biomass, separate from the lignocellulosic biomass, or a combination thereof; b) adding heat to the pretreatment reactor such that said lignocellulosic biomass and acid are heated for a time and at a temperature sufficient to provide a slurry comprising pretreated lignocellulosic biomass, said slurry disposed within the pretreatment reactor adjacent a headspace, said headspace comprising sulfur dioxide; c) removing the slurry from the pretreatment reactor; d) reserving at least a portion of the sulfur dioxide in the headspace within at least one of the pretreatment reactor and a reservoir connected to the pretreatment reactor as the slurry is removed from the pretreatment reactor; and e) pretreating additional lignocellulosic biomass in the presence of the reserved sulfur dioxide.

One aspect of the present disclosure is directed to a process for hydrolyzing lignocellulosic biomass comprising: a) feeding lignocellulosic biomass into a pretreatment reactor, said pretreatment reactor provided with a charge of sulfur dioxide used in a previous pretreatment of lignocellulosic biomass; b) feeding acid into the pretreatment reactor, said acid comprising at least one of sulfur dioxide and sulfurous acid, said acid added to the pretreatment reactor with the lignocellulosic biomass, separate from the lignocellulosic biomass, or a combination thereof; c) heating the lignocellulosic biomass disposed in the pretreatment reactor for a time and at a temperature sufficient to provide a slurry comprising pretreated lignocellulosic biomass, said slurry adjacent a headspace comprising sulfur dioxide; d) preventing at least a portion of the sulfur dioxide in the headspace from exiting the pretreatment reactor as the slurry is discharged; and e) hydrolyzing cellulose in the slurry in the presence of cellulase to produce glucose.

One aspect of the present disclosure is directed to a process for hydrolyzing lignocellulosic biomass comprising: a) feeding lignocellulosic biomass into a pretreatment reactor through a loading valve, said pretreatment reactor connected to a vapour reservoir through a reservoir valve; b) closing the loading valve; c) feeding at least one of steam, sulfur dioxide, and sulfurous acid into the pretreatment reactor with the loading valve closed, thereby increasing a pressure in the pretreatment reactor; d) heating the lignocellulosic biomass disposed in the pretreatment reactor for a time and at a temperature sufficient to provide a slurry comprising pretreated lignocellulosic biomass, said heating conducted with the reservoir valve open; e) closing the reservoir valve such that sulfur dioxide gas is confined to the vapour reservoir; f) opening a discharge valve such that the slurry is discharged from the pretreatment reactor while the sulfur dioxide in the vapour reservoir remains in the vapour reservoir; g) closing the discharge valve and loading another batch of lignocellulosic biomass into the reactor through the loading valve; h) closing the loading valve; i) opening the reservoir valve; j) feeding at least one of steam, sulfur dioxide, and sulfurous acid into the pretreatment reactor; and k) hydrolyzing cellulose from the discharged slurry in the presence of cellulase to produce glucose.

One aspect of the present disclosure is directed to a process for hydrolyzing lignocellulosic biomass comprising a) feeding lignocellulosic biomass and acid into a pretreatment reactor, said acid comprising at least one of sulfur dioxide and sulfurous acid; b) heating said lignocellulosic biomass in the pretreatment reactor for a time and at a temperature sufficient to provide a slurry comprising pretreated lignocellulosic biomass, said slurry adjacent a headspace comprising sulfur dioxide; c) removing at least a portion of said slurry from the pretreatment reactor; d) preventing at least a portion of the sulfur dioxide in the headspace from exiting the pretreatment reactor as the at least a portion of the slurry is removed such that a concentration of sulfur dioxide in at least a region of the headspace of the pretreatment reactor is substantially maintained while the slurry is removed; e) hydrolyzing cellulose in the removed slurry in the presence of cellulase to produce glucose; and f) selecting an amount of make-up sulfur dioxide to be added to the pretreatment reactor in dependence upon an amount of sulfur dioxide prevented from exiting the pretreatment reactor.

DETAILED DESCRIPTION

Figure 1:
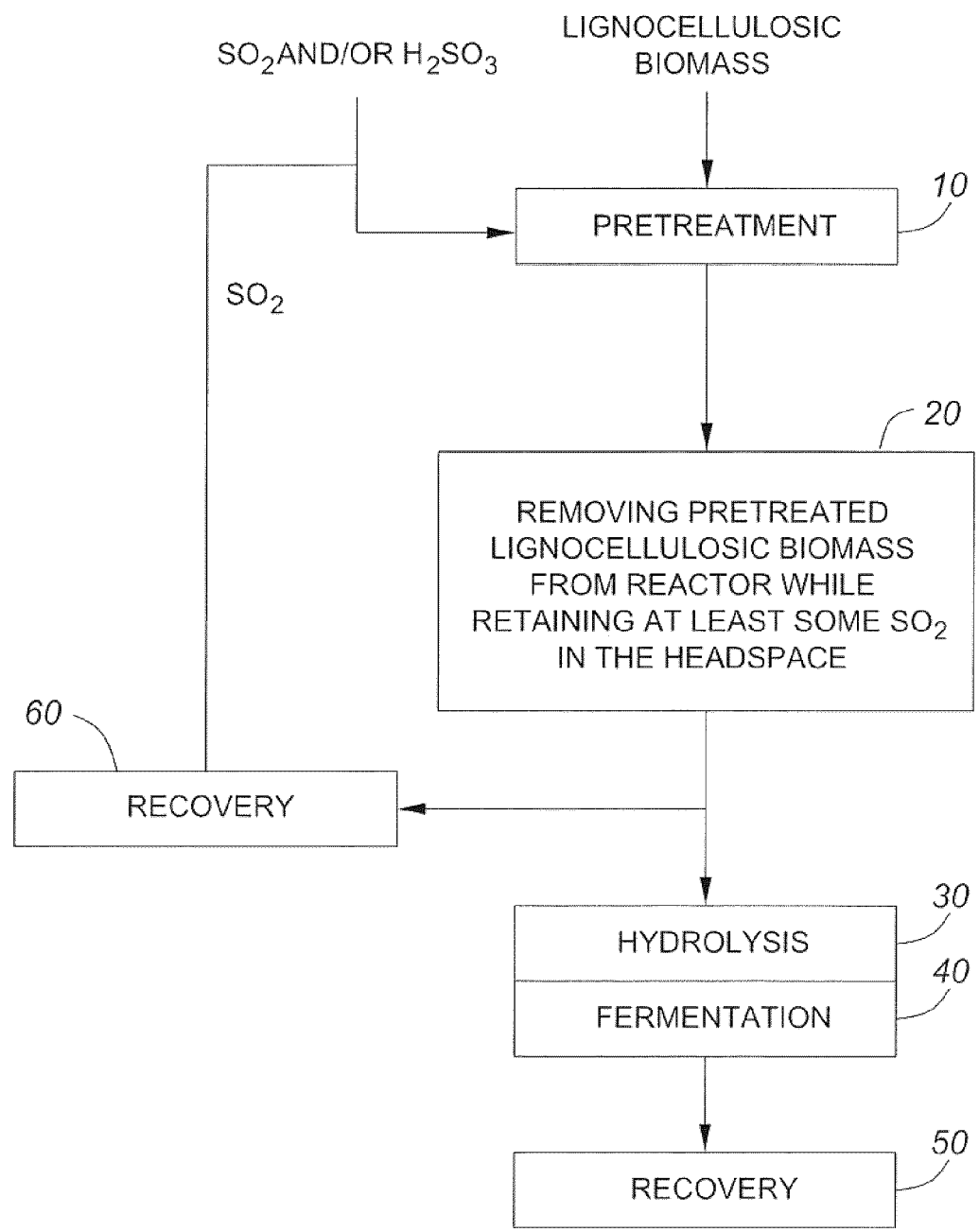
FIG. 1 is a block flow diagram of a method according to one embodiment of the invention.

Certain exemplary embodiments of the invention now will be described in more detail, with reference to the drawings, in which like features are identified by like reference numerals. The invention may, however, be embodied in many different forms and should not be construed as limited to the embodiments set forth herein.

The terminology used herein is for the purpose of describing certain embodiments only and is not intended to be limiting of the invention. For example, as used herein, the singular forms "a," "an," and "the" may include plural references unless the context clearly dictates otherwise. The terms "comprises", "comprising", "including", and/or "includes", as used herein, are intended to mean "including but not limited to." The term "and/or", as used herein, is intended to refer to either or both of the elements so conjoined. The term "between" as used herein in the context of ranges is intended to include the endpoints of the indicated ranges, for example, a value that is "between 2 and 5" includes not only the intermediate values but the endpoints "2" and "5" as well. The phrase "at least one" in reference to a list of one or more elements, is intended to refer to at least one element selected from any one or more of the elements in the list of elements, but not necessarily including at least one of each and every element specifically listed within the list of elements. Thus, as a non-limiting example, the phrase "at least one of A and B" may refer to at least one A with no B present, at least one B with no A present, or at least one A and at least one B in combination. The terms "first", "second", etc., may be used to distinguish one element from another, and these elements should not be limited by these terms. Unless defined otherwise, all technical and scientific terms used herein have the same meanings as commonly understood by one of ordinary skill in the art.

Referring to FIG. 1, there is shown a flow diagram of a process in accordance with one embodiment of the invention. Lignocellulosic biomass is fed to a pretreatment 10 that produces pretreated biomass. The pretreatment 10 is conducted in a pretreatment system that includes a pressurizable reactor or pretreatment reactor. The lignocellulosic biomass is added to the pretreatment reactor at a rate and/or in an amount such that a headspace is present within the reactor when closed and/or pressurized. The pretreatment is an acid-catalyzed pretreatment that includes heating the lignocellulosic biomass in the presence of the acid. The acid, which may be added to the lignocellulosic biomass in the pretreatment reactor and/or upstream of the pretreatment reactor, is typically sulfur dioxide ($SO_2$) and/or sulfurous acid ($H_2SO_3$), the latter of which is sulfur dioxide dissolved in water. In general, the acid may be fed to the pretreatment reactor with the lignocellulosic biomass (i.e., through the same inlet and at approximately the same time) and/or separately from the lignocellulosic biomass (i.e., through different inlets, or through the same inlet but at different times). For example, with regard to the former, the acid and/or lignocellulosic biomass may be fed to the pretreatment reactor as sulfur dioxide impregnated lignocellulosic biomass, as a sulfurous acid/lignocellulosic biomass slurry, or as sulfur dioxide injected into the pretreatment system upstream of the pretreatment reactor that is allowed to flow into the pretreatment reactor with the lignocellulosic biomass. In one embodiment, the acid is added in an amount to provide a predetermined sulfur dioxide loading or a total sulfur dioxide loading in a predetermined range. In general, the sulfur dioxide loading is described as a weight percent of sulfur dioxide on dry weight of lignocellulosic biomass fed to the pretreatment reactor. Once the acidified lignocellulosic biomass has resided within the pretreatment reactor for a time (e.g., the residence time) and at a temperature (e.g., a pretreatment temperature or temperature range) that provides the desired degree of pretreatment, the resulting slurry containing the pretreated lignocellulosic biomass composition is removed from the pretreatment reactor 20.

In general, the slurry containing the pretreated lignocellulosic biomass is removed 20 from the pretreatment reactor while retaining at least some sulfur dioxide from the headspace. The headspace, which generally refers to the space in the pretreatment reactor above and/or around the slurry, includes all space within the pretreatment reactor or pretreatment system that the sulfur dioxide vapours are free to fill when the pretreatment reactor is pressurized (e.g., including the space in vapour reservoirs that are part of, or are in fluid connection with, the pretreatment reactor).

In one embodiment, the pretreated lignocellulosic biomass is removed 20 through a discharge valve into a flash tank such that a volatile portion of the pretreated biomass composition flashes off in a flash stream, while the condensate portion is cooled.

The cooled pretreated biomass composition (e.g., the condensate portion) is fed to hydrolysis 30 followed by an optional fermentation 40, or is fed to a combined hydrolysis/fermentation 30/40. The hydrolysis 30 converts cellulose in the pretreated biomass composition to glucose, while the fermentation 40 converts at least a portion of the glucose to a fermentation product (e.g., ethanol, butanol, acetic acid, etc.). The fermentation product may be recovered in the optional recovery step 50 (e.g., distillation if the fermentation product is ethanol).

The flash stream, which may include steam and/or sulfur dioxide, is optionally fed to one or more recovery stages 60, wherein the energy from the steam is recovered and/or recycled and/or wherein the sulfur dioxide is recovered and/or recycled. For example, in one embodiment, the one or more recovery stages includes a sulfur dioxide recovery system that provides sulfur dioxide and/or sulfurous acid in a form suitable for recycling back into the pretreatment 10. Whether the pretreatment is operated in batch mode or continuous mode, the sulfur dioxide from sulfur dioxide recovery and/or the sulfur dioxide introduced into the pretreatment reactor after the continuous pretreatment has started or after the first batch has been completed, may be referred to as makeup sulfur dioxide.

In one embodiment, at least a portion of the sulfur dioxide in the headspace is retained while the pretreated lignocellulosic biomass is removed 20 through the discharge valve, by actively closing off (e.g., isolating) a portion of the headspace. For example, in one embodiment, a portion of the headspace provided by a vapour reservoir chamber is sealed off with a valve. In another embodiment, at least a portion of the sulfur dioxide in the headspace is retained by maintaining a liquid seal between the headspace and the discharge valve.

Advantageously, since a portion of the sulfur dioxide is retained in the pretreatment reactor while the pretreated lignocellulosic material is discharged, a smaller amount of make-up sulfur dioxide may be required to provide the desired $SO_2$ concentration within the pretreatment reactor and/or to replenish sulfur dioxide in the headspace. In one embodiment, the concentration of sulfur dioxide in the headspace may be maintained using only a small fraction of the makeup sulfur dioxide.

Lignocellulosic Biomass

The lignocellulosic biomass fed to the pretreatment 10 may include and/or be derived from any lignocellulosic feedstock.

In general, lignocellulosic feedstock refers to any type of feedstock containing cellulose, hemicellulose, and lignin. In one embodiment, the combined content of cellulose, hemicellulose and lignin is greater than 25 wt %. In one embodiment, sucrose, fructose, and/or starch are also present, but in lesser amounts than cellulose and hemicellulose.

Some examples of lignocellulosic feedstock include: (i) energy crops; (ii) residues, byproducts or waste from the processing of plant biomass in a facility or feedstock derived therefrom; (iii) agricultural residues; (iv) forestry biomass; (v) waste material derived from pulp and paper products; (vi) pulp and paper waste; and/or (vii) municipal waste including components removed from municipal waste.

Energy crops include biomass crops such as grasses, including C4 grasses, such as switch grass, energy cane, sorghum (including sweet sorghum), cord grass, rye grass, miscanthus, reed canary grass, C3 grasses such as *Arundo donax* or a combination thereof.

Residues, byproducts or waste from the processing of plant biomass in a facility of feedstock derived therefrom include residues remaining after obtaining sugar from plant biomass such as sugar cane bagasse, sugar cane tops and leaves, beet pulp, or residues remaining after removing sugar from Jerusalem artichoke or residues remaining after grain processing, such as corn fiber, corn stover, or bran from grains. Agricultural residues include, but are not limited to soybean stover, corn stover, rice straw, sugar cane tops and/or leaves, rice hulls, barley straw, corn cobs, wheat straw, canola straw, oat straw, oat hulls, corn fiber and corn cobs.

Forestry biomass includes recycled wood pulp fiber, sawdust, hardwood, softwood, trimmings and/or slash from logging operations. Pulp and paper waste includes waste from chemical pulping such as black liquor, spent sulfite liquor, sludge and/or fines.

Municipal waste includes post-consumer material or waste from a variety of sources such as domestic, commercial, institutional and/or industrial sources. For example, the term includes refuse from waste collection and/or sewage sludge.

Lignocellulosic feedstock can be a mixture of fibers that originate from different kinds of plant materials, including mixtures of cellulosic and non-cellulosic feedstocks.

In one embodiment, the lignocellulosic feedstock is (i) an energy or biomass crop, (ii) an agricultural residue, and/or (iii) hardwood. In one embodiment, the lignocellulosic feedstock is a non-woody lignocellulosic feedstock such as (i) an energy crop, (ii) residues, byproducts or waste from processing of plant biomass or feedstock derived therefrom in a facility, and/or (iii) agricultural residues. In one embodiment, the lignocellulosic feedstock is a non-woody lignocellulosic feedstock such as (i) an energy crop and/or (ii) an agricultural residue. In one embodiment, the lignocellulosic feedstock is straw, stover, or an energy crop. As used herein, straw refers to the stem, stalk and/or foliage portion of crops remaining after the removal of starch and/or sugar containing components for consumption. Examples of straw include, but are not limited to sugar cane tops and/or leaves, bagasse, oat straw, wheat straw, rye straw, oat straw, rice straw and barley straw. Stover includes the stalk and foliage portion of crops after the removal of starch and/or sugar containing components of plant material for consumption. Examples of stover include, but are not limited to, soybean stover, sorghum stover and corn stover.

Biomass Preparation

In general, the lignocellulosic biomass may be treated in one or more optional preparatory steps prior to pretreatment 10 and/or as part of the pretreatment 10. Some examples of biomass preparation include size reduction, washing, slurry formation, wetting, soaking, dewatering, plug formation, addition of heat, and addition of chemicals (e.g., pretreatment and/or other). In general, these preparatory treatments may depend on the type of biomass and/or selected pretreatment conditions.

In one embodiment, the lignocellulosic biomass is subjected to a size reduction. Some examples of size reduction methods include milling, grinding, agitation, shredding, compression/expansion, and/or other types of mechanical action. Size reduction by mechanical action may be performed by any type of equipment adapted for the purpose, for example, but not limited to, hammer mills, tub-grinders, roll presses, refiners, and hydrapulpers. In one embodiment, lignocellulosic feedstock having an average particle size that is greater than about 6-8 inches is subject to a size reduction wherein at least 90% by volume of the particles produced from the size reduction have a length between about 1/16 inch and about 6 inches. Some examples of suitable size reductions and/or equipment are described in WO 2006/026863.

In one embodiment, the lignocellulosic biomass is washed and/or leached with a liquid (e.g. water or an aqueous solution). Washing, which may be performed before, during, or after size reduction, may remove sand, grit, fine particles of the lignocellulosic feedstock, and/or other foreign particles that otherwise may cause damage to the downstream equipment. Leaching, which may also be performed before, during, or after size reduction, may remove soluble compounds from the lignocellulosic feedstock. For example, in one embodiment, the lignocellulosic feedstock is leached with water or an aqueous solution (e.g., wherein the biomass is in contact with the liquid for more than about 2 minutes) in order to remove salts and/or buffering agents. In one embodiment, the lignocellulosic biomass is leached as set forth in WO 02/070753 to Griffin, which is incorporated herein by reference. Alternatively, or additionally, sand may be removed using other wet or dry sand removal techniques that are known in the art (e.g., including the use of a hydrocyclone or a sieve).

In one embodiment, the biomass is slurried in liquid (e.g., water), which allows the biomass to be pumped. In one embodiment, the biomass is slurried subsequent to size reduction, washing, and/or leaching. The desired weight ratio of water to dry biomass solids in the slurry may be determined by factors such as pumpability, pipe-line requirements, and other practical considerations. For example, in one embodiment, the biomass is slurried to provide a consistency between about 1 wt % and about 40 wt %, or about 1 wt % and about 20 wt %, or between about 4 wt % and about 10 wt %.

In one embodiment, the biomass is wet and/or soaked in a liquid (e.g., water, an aqueous solution). For example, in one embodiment the biomass is soaked in an aqueous solution comprising a pretreatment chemical. In one embodiment, the biomass is soaked subsequent to being slurried (e.g., the slurried biomass is fed to a soaking tank). Feeding the slurried biomass to a soaking tank may allow pretreatment chemical(s) to more uniformly impregnate the biomass, which in turn may provide even cooking in the pretreatment. For example, soaking the feedstock in a solution comprising a pretreatment chemical (e.g., such as sulfuric acid and/or sulfurous acid) typically provides uniform impregnation of the biomass with the pretreatment chemical. Wetting and/or soaking the feedstock with water, may allow gaseous pretreatment chemicals (e.g., comprising sulfur dioxide) to more uniformly and/or completely impregnate the biomass during subsequent chemical addition steps. In particular, soaking the feedstock in water, followed by dewatering and sulfur dioxide introduction, may provide a uniform acid impregnation. In general, uniform impregnation may ensure that some material is not overcooked and/or degraded due to high localized concentration of the pretreatment chemical, and/or that some material is not undercooked (e.g., which may result in low xylose yield and incomplete cellulose hydrolysis). Undercooking or overcooking of lignocellulosic feedstock may be particularly problematic when the pretreatment is conducted under medium or high solids consistency since the non-uniformity in the concentration of the pretreatment chemical and the temperature may be more pronounced.

Soaking is typically conducted in a tank and/or other suitable equipment for handling soaked material. In one embodiment, soaking is conducted at a relatively low consistency (e.g., between about 1 wt % and about 20 wt %, or about 2 wt % and about 18 wt %, or between about 3 wt % and about 15 wt %). In general, soaking may be carried out at any suitable temperature and/or for any suitable duration. For example, in one embodiment, soaking is conducted at a temperature between about 20° C. and about 80° C. and/or for a duration in the range between about 1 minute and about 30 minutes, or longer. In one embodiment, the water or aqueous solution is provided from a recycle stream obtained from other stages of the process. In one embodiment, soaking is conducted in one or more batch or continuous vessels, or a combination thereof, each of which may be a mixed vessel or an unmixed vessel.

In one embodiment, the lignocellulosic biomass is at least partially dewatered to increase the undissolved solids content relative to the incoming biomass. For example, in one embodiment, the lignocellulosic feedstock is at least partially dewatered to provide a predetermined consistency and/or a predetermined moisture level. In general, the term consistency refers the amount of undissolved dry solids or "UDS" in a sample, and is often expressed as a ratio on a weight basis (wt:wt), or as a percent on a weight basis, for example, % (w/w), also denoted herein as wt %. For example, consistency may be determined by filtering and washing the sample to remove dissolved solids and then drying the sample at a temperature and for a period of time that is sufficient to remove water from the sample, but does not result in thermal degradation of the sample. After water removal, or drying, the dry solids are weighed and the weight of water in the sample is the difference between the weight of the sample and the weight of the dry solids. Providing lignocellulosic biomass with a higher consistency to pretreatment may advantageously reduce heating requirements during pretreatment (e.g., since there is less liquid to heat).

In one embodiment, the lignocellulosic biomass is at least partially dewatered in order to remove at least some of the liquid introduced during washing, leaching, slurrying, and/or soaking. In one embodiment, wherein the biomass is subject to dewatering after being slurried and/or after soaking, the water expressed from the biomass in dewatering is recycled back to the slurrying and/or soaking steps.

In one embodiment, dewatering is achieved using a drainer, filtration device, screen, screw press, extruder, or a combination thereof. In one embodiment, dewatering is achieved using a centrifuge. In one embodiment, the dewatering is achieved prior to and/or as part of plug formation. Without being limiting, a plug formation device incorporating a dewatering section may be a pressurized screw press or a plug screw feeder, as described in WO 2010/022511, which is incorporated herein by reference.

In general, dewatering includes removing water from the biomass at any pressure (e.g., under pressure or at atmospheric pressure). In one embodiment, wherein the lignocellulosic biomass is subjected to dewatering under pressure, the pressure increase may be caused by one or more high pressure pumps. The pump, or other feeding device, may increase the pressure of the lignocellulosic biomass prior to dewatering (e.g., from about 50 psig to about 900 psig, or about 70 psig to about 800 psig or about 140 psig to about 700 psig). The pressure may be measured with a pressure sensor located at a biomass inlet port on a dewatering device or a plug formation device that also dewaters the feedstock. Alternatively, the feedstock subjected to dewatering may be at atmospheric pressure, or at a pressure below about 50 psig. Dewatering at atmospheric pressure is generally convenient if the lignocellulosic biomass is being fed to a batch pretreatment reactor, whereas dewatering under pressure may be more suitable in embodiments where the lignocellulosic biomass is being fed to a continuous pretreatment reactor.

In one embodiment, the biomass (e.g., which may or may not have been subject to a previous dewatering) is subject to plug formation. In general, plug formation may be considered an integration of lignocellulosic biomass particles into a compacted mass referred to herein as a plug. Plug formation devices may or may not form a plug that acts as a seal between areas of different pressure. In one embodiment, a plug formation device is provided at the front end of the pressurized pretreatment reactor. In one embodiment, the biomass is fed to a plug formation device that dewaters the biomass and/or is disposed downstream of a dewatering device. In one embodiment, the plug formation device that dewaters the biomass includes a housing or shell with openings through which water can pass. Some examples of plug formation devices that dewater biomass include a plug screw feeder, a pressurized screw press, a co-axial piston screw feeder, and a modular screw device.

In one embodiment, the dewatered biomass may have a weight ratio of water to undissolved dry solids between about 0.5:1 (67 wt % dry solids) and about 5:1 (17 wt % dry solids), or between about 1:1 (50 wt % dry solids) and about 4:1 (20 wt % dry solids), or between about 1.5:1 (40 wt % dry solids) to about 4:1 (20 wt % dry solids), or between about 1.5:1 (40 wt % dry solids) and about 3.5:1 (22 wt % dry solids).

In one embodiment, the lignocellulosic biomass is subjected to heat (e.g., applying extraneous heat, a hot liquid, and/or steam) prior to the lignocellulosic biomass entering the pretreatment reactor. In one embodiment, the biomass is heated as part of the soaking step, as part of a leaching step, or as a separate step. In one embodiment, the biomass is subjected to a steam addition step upstream of entering the pretreatment reactor. For example, in one embodiment, the dewatered biomass is fed to a downstream "heating chamber" or "high shear heating chamber" prior to being fed to a pretreatment reactor. For example, the heating chamber, which may be a horizontally-oriented or essentially horizontally-oriented elongate chamber, may include disintegrating elements for disintegrating the plug of biomass into particles and/or may include inlets for direct steam injection (e.g., to preheat the biomass and provide efficient heat transfer) and/or adding pretreatment chemicals. For example, in one embodiment, a pretreatment chemical such as sulfur dioxide may also be added during direct steam injection in the heating chamber. In one embodiment, the biomass is preheated prior to being fed to the pretreatment reactor using a heating chamber as disclosed, for example, in U.S. Publication No. 2013/0071903, which is hereby incorporated by reference. In one embodiment, the operating pressure and temperature of the heating chamber corresponds to the pressure and temperature of the downstream pretreatment reactor. In one embodiment, the biomass is resident in the heating chamber for a duration between about 1 second and about 120 seconds, or longer.

As described above, each of the washing, leaching, slurrying, soaking, dewatering, and preheating stages are optional and may or may not be included in the process. In general, if the process is a continuous-flow process, it may be advantageous to include steps of slurrying and dewatering prior to pretreatment in order to improve process economics and efficiency. In addition, providing soaking, preheating, and chemical addition steps, upstream of the pretreatment reactor may provide a more uniform and/or efficient pretreatment. In any case, one or more additional steps/devices may also be provided. For example, without being limiting, examples of such devices include mechanical restricting devices, restraining devices, scrapers and conveyors. For example, in one embodiment, a component and/or device is provide downstream and/or as part of the plug formation device that breaks the plug into segments as it is discharged from the plug formation device, or into other devices positioned downstream of the plug formation device (e.g., into a heating chamber).

Pretreatment

In general, pretreatment refers to one or more steps wherein the lignocellulosic biomass is treated such that the fiber structure thereof is disrupted and the cellulose in the lignocellulosic biomass is made more susceptible and/or accessible to enzymes in a subsequent hydrolysis.

In one embodiment, pretreatment 10 includes feeding the lignocellulosic biomass into a pretreatment reactor, wherein it resides for a time (i.e., residence time) at a temperature (e.g., or within a predetermined temperature range) selected to provide the desired level and/or degree of pretreatment.

In general, the pretreatment reactor may be part of a pretreatment system, which may include a plurality of components/devices in addition to the pretreatment rector. Some examples of these devices/components include a biomass conveyer, washing system, dewatering system, a plug formation device, a heating chamber, a high shear heating chamber, a pre-steaming chamber, an acid impregnation chamber, vapour reservoir chamber, a second pretreatment reactor, connecting conduits, valves, pumps, etc. For example, in one embodiment, the pretreatment system includes a high shear heating chamber and a pretreatment reactor. In general, the pretreatment system may be formed from different devices/components that are connected in the desired sequence and/or may be constructed such that different devices/components are integrated.

In general, the pretreatment reactor and/or pretreatment system is pressurizable. For example, in one embodiment, the pretreatment reactor and/or pretreatment system includes a plurality of valves and/or other pressure increasing, pressure decreasing, or pressure maintaining components for providing and/or maintaining the pretreatment reactor at predetermined pressure (e.g., greater than about 90 psia and less than about 680 psia). The devices/components within the pretreatment system may be held at a same pressure or may be held at different pressures. For example, in one embodiment, the pretreatment system includes a pressurized screw feeder, a high shear heating chamber, a pretreatment reactor, and a discharge valve (e.g., blow-valve), disposed in sequence, all of which are in fluid communication such that the system pressure between the output of the pressurized screw feeder and the discharge valve is constant. In another embodiment, at least one of the devices/components is held at a different pressure.

In general, the pretreatment reactor and/or pretreatment system may include a heater, or some other heating means, for heating the lignocellulosic biomass (e.g., to the pretreatment temperature). For example, in one embodiment, the pretreatment reactor is clad in a heating jacket. In another embodiment, the pretreatment reactor and/or the pretreatment system includes direct steam injection inlets. In one embodiment, the lignocellulosic biomass is heated (e.g., directly or indirectly) in the pretreatment reactor. In another embodiment, the lignocellulosic biomass is heated before entering the pretreatment reactor (e.g., in an upstream heating chamber). In one embodiment, the lignocellulosic biomass is heated both upstream and in the pretreatment reactor. In any case, direct steam injection may be advantageous in terms of quickly and uniformly heating high consistency biomass and/or for breaking down the biomass structure via steam explosion. In one embodiment, the lignocellulosic material is heated to a temperature greater than about 120° C. For example, in one embodiment, the pretreatment temperature is between about 170° C. and about 300° C., between about 180° C. and about 280° C., and/or between about 185° C. and about 240° C. In one embodiment, the pretreatment temperature is above about 190° C. In practice, there may be a time delay between the time at which the heating process is started and the time when the biomass reaches the predetermined pretreatment temperature/temperature range.

In general, the pretreatment is conducted under acidic conditions (i.e., in the presence of sulfur dioxide and/or sulfurous acid, although other acids, such as sulfuric acid, may be also present). In one embodiment, the pretreatment reactor and/or pretreatment system includes one or more inlets for adding acid into the pretreatment system. For example, in one embodiment, sulfur dioxide and/or sulfurous acid is injected into the pretreatment reactor such that the lignocellulosic biomass and the acid are added separately (i.e., separate inlets). In another embodiment, the lignocellulosic biomass is impregnated with sulfur dioxide and/or sulfurous acid (and optionally another acid such as sulfuric acid) upstream of the pretreatment reactor, such that at least a portion of the sulfur dioxide and/or sulfurous acid is added to the pretreatment reactor with the lignocellulosic biomass (i.e., through the same inlet). In one embodiment, the sulfur dioxide and/or sulfurous acid is added to the lignocellulosic biomass during a soaking step, prior to or after dewatering, prior to or after plug formation, into a heating chamber, into the plug formation device, into the pretreatment reactor, or any combination thereof. For example, in one embodiment, the lignocellulosic biomass is soaked in aqueous sulfurous acid solution, whereas in another embodiment, the lignocellulosic biomass is soaked in water and sulfur dioxide is added to the soaked and at least partially dewatered lignocellulosic biomass in the heating chamber and/or pretreatment reactor. In one embodiment, acid is added to lignocellulosic biomass prior to it entering the pretreatment reactor, and not in the pretreatment reactor.

The addition of acid (e.g., sulfur dioxide and/or sulfurous acid) to the lignocellulosic biomass, at one or more than one point in the process, provides acidified lignocellulosic biomass. The term "acidified lignocellulosic biomass" refers to the fact that the pH of a sample from the lignocellulosic biomass corresponds to acidic conditions, and is not intended to indicate whether or not a reaction between the acid and the lignocellulosic biomass occurs.

In general, the acidified lignocellulosic biomass will reside within the pretreatment reactor for a time referred to as the residence time or pretreatment time. In general, the residence time does not typically include the time required to ramp the temperature of the lignocellulosic biomass up to the pretreatment temperature (e.g., starting temperature if a temperature range). For example, in one embodiment, the residence time is the time that the lignocellulosic material is heated above a predetermined temperature (e.g., above 170° C.). The time that the biomass is held at the pretreatment temperature or within the pretreatment temperature range may be dependent on the type of feedstock, the amount of pretreatment chemicals, and/or the desired degree of pretreatment. In one embodiment, the degree of pretreatment is selected to convert most of the hemicellulose component to soluble sugars (e.g., xylose, mannose, arabinose, and glucose), but little of the cellulose component to sugars (e.g., which may be hydrolyzed in a subsequent enzymatic hydrolysis). For example, in one embodiment, the degree of pretreatment is selected such that the amount of xylan hydrolyzed to xylose is greater than about 50 wt %, about 60 wt %, about 70 wt %, about 80 wt %, or about 90 wt %. In one embodiment, the level of pretreatment is selected to minimize sugar degradation products such as furfural and 5-hydroxymethyl furfural (HMF), which are potential enzymatic hydrolysis inhibitors. In one embodiment, the residence time will be less than about 60 minutes. In one embodiment, the residence time will be less than about 30 minutes. In one embodiment, the residence time will be less than about 10 minutes. In one embodiment, the residence time will be less than 7 minutes. In general, providing a residence time that is greater than about 1 minutes and less than about 10 minutes may be advantageous in terms of providing an efficient pretreatment without the production of a large number of potentially inhibitory sugar degradation products.

In one embodiment, sufficient acid is added to provide a pH less than about 4. In another embodiment, sufficient acid is added to provide a pH less than about 1.5. In another embodiment, sufficient acid is added to provide a pH close to about 1.

In one embodiment, sufficient acid is added to provide a sulfur dioxide loading and/or equivalent sulfur dioxide loading of at least 1 wt % (e.g., weight of sulfur dioxide on weight of dry lignocellulosic biomass). In one embodiment, sufficient acid is added to provide a sulfur dioxide loading and/or equivalent sulfur dioxide loading in an amount of at least 5 wt % (e.g., weight of sulfur dioxide on weight of dry lignocellulosic biomass). In one embodiment, sufficient acid is added to provide a sulfur dioxide loading and/or equivalent sulfur dioxide loading in an amount of at least 12 wt % (e.g., weight of sulfur dioxide on weight of dry lignocellulosic biomass). In one embodiment, sufficient acid is added to provide a sulfur dioxide loading and/or equivalent sulfur dioxide loading in an amount of at least 15 wt % (e.g., weight of sulfur dioxide on weight of dry lignocellulosic biomass). The phrase "sulfur dioxide loading" is used to describe the amount of sulfur dioxide added per amount of lignocellulosic biomass added as calculated from the total grams of sulfur dioxide per gram of dry lignocellulosic biomass as a percentage (e.g., wt %). The term "equivalent sulfur dioxide loading" is used to describe the theoretical amount of sulfur dioxide added per given amount of lignocellulosic biomass, calculated from the grams of sulfur dioxide or sulfurous acid expressed as equivalent sulfur dioxide provided per gram of dry lignocellulosic biomass. Notably, when there is a headspace in the pretreatment reactor in which a charge of sulfur dioxide may be maintained and/or in which a portion of the sulfur dioxide loaded into the pretreatment reactor may be isolated from the discharge valve, the amount of sulfur dioxide available for the pretreatment (e.g., weight of sulfur dioxide on weight of dry lignocellulosic biomass) may be higher than the sulfur dioxide loading.

In general, the pretreatment efficiency is typically at least partially dependent on the equivalent sulfur dioxide loading and/or concentration of sulfur dioxide in the pretreatment reactor. For example, larger amounts of sulfur dioxide and/or sulfurous acid may correspond to a more effective cook. The concentration of sulfur dioxide in the pretreatment reactor is dependent on the amount of sulfur dioxide and/or sulfurous acid in solution and in the gas phase. More specifically, the sulfur dioxide available for pretreatment includes sulfur dioxide and/or sulfurous acid present in solution and in the vapour space, and thus may be affected by the headspace.

The term "headspace", as used herein, refers to the space in the sealed pretreatment reactor and/or system above and/or around the biomass (e.g. the biomass slurry). For example, if the biomass slurry has a relatively low consistency (e.g., 6 wt %), the headspace includes the space in the pretreatment reactor above the liquid level, whereas if the biomass slurry has a relatively high consistency (e.g., 35-67 wt %, and thus may be supported in a basket or bale within the pretreatment reactor), the headspace includes the space in the pretreatment reactor that is above and/or around the biomass slurry. Notably, in each case, the headspace may include space within one or more vapour reservoirs that are part of, or are in fluid connection with, the pretreatment reactor.

The term "vapour space", as used herein, refers to both the headspace and the void space in the biomass slurry. For example, if the biomass slurry has a relatively low consistency (e.g., below 15 wt %), the void space may include gas pockets or bubbles in the slurry, whereas if the biomass slurry has a higher consistency (e.g., above 15 wt %), the void space may include gas pockets, gas bubbles, and/or the space between wet particles. Advantageously, the vapour space may contain sulfur dioxide used to drive the pretreatment forward and/or provide a more efficient pretreatment. For example, the vapour space may contain sulfur dioxide that replaces sulfur dioxide, sulfurous acid, and/or the corresponding dissociation products, consumed by the pretreatment (e.g., to form lignosulfonates and/or other sulfonic acids) as the pretreatment progresses.

The sulfur dioxide in the vapour space may originate from the decomposition of sulfurous acid (e.g., which may be envisaged as $H_2SO_{3(aq)} \rightarrow H_2O_{(l)} SO_{2(g)}$), from the liberation of sulfur dioxide impregnated in the lignocellulosic biomass, and/or from sulfur dioxide gas injected into the pretreatment system. In any case, the sulfur dioxide in the vapour space may originate from sulfurous acid and/or sulfur dioxide introduced directly into the pretreatment reactor and/or upstream of the pretreatment reactor. For example, the sulfur dioxide in the vapour space may arise solely from sulfur dioxide and/or sulfurous acid used for impregnating the lignocellulosic material before it enters the pretreatment reactor. Alternatively, the sulfur dioxide in the vapour space may arise primarily from the addition of sulfur dioxide gas. Although sulfur dioxide is soluble in water (e.g., forming a sulfurous acid solution), the concentration in solution decreases with increasing temperature due to the volatility of sulfur dioxide (e.g., which has an atmospheric boiling point of about $-10°$ C.). Therefore, the concentration in solution decreases with increasing temperature. In fact, at most pretreatment temperatures, a relatively large amount of the sulfur dioxide will be in the vapour space.

Although providing a relatively large charge of sulfur dioxide in the vapour space may improve pretreatment, the cost may be relatively high. For example, consider a batch process, wherein a batch of lignocellulosic biomass is fed to the reactor, is treated, and is discharged before a new batch of lignocellulosic biomass is fed to the reactor. In this type of conventional batch pretreatment, the unreacted sulfur dioxide/sulfurous acid are fully discharged from the pretreatment reactor with the pretreated biomass, including the excess sulfur dioxide in the headspace. Accordingly, the full makeup amount of sulfur dioxide and/or sulfurous acid is required for the next batch of lignocellulosic biomass.

In addition, in many embodiments, it is advantageous to provide a reasonably sized headspace. For example, it may be advantageous to provide a reasonably sized headspace in a batch reactor because the sulfur dioxide in the headspace, which is in equilibrium with the sulfur dioxide/sulfurous acid in the stuffy, may replenish sulfur dioxide/sulfurous acid consumed during the pretreatment. In a continuous pretreatment system, a reasonably sized headspace may be present as a result of the desired fill/operating level of the pretreatment reactor. When all of the unreacted sulfur dioxide present in the headspace is discharged with the pretreated biomass, a relatively large amount of sulfur dioxide may need to be recovered and the makeup amount of sulfur dioxide and/or sulfurous acid may be significant.

In addition, in embodiments wherein the headspace is relatively large (e.g., greater than about 50% (v/v) of the pretreatment reactor), the equivalent sulfur dioxide loading may need to be increased since the concentration of the sulfur dioxide in the headspace and/or the equilibrium relationships may also need to be considered. Accordingly, when the pretreated biomass, sulfur dioxide, and/or sulfurous acid are discharged into a flash tank, the relatively large amount of sulfur dioxide in the resulting flash stream may need to be recovered (e.g., for environmental and/or economic reasons), thus further adding to the costs.

In accordance with one embodiment of the instant invention, at least a portion of the sulfur dioxide in the headspace is prevented from exiting the pretreatment reactor as the pretreated lignocellulosic biomass is removed from the pretreatment reactor. Advantageously, this reserved sulfur dioxide may be reused in the pretreatment of additional lignocellulosic biomass (e.g., without any purification, recovery, and/or external recycling). For example, if the pretreatment reactor is operated in batch mode, then this additional amount of lignocellulosic biomass may correspond to the subsequent batch of lignocellulosic biomass. If the pretreatment reactor is operated in continuous mode (e.g., wherein biomass is fed to the reactor, is treated, and is discharged while new biomass is being fed to the reactor), then this additional amounts of lignocellulosic biomass may correspond to biomass that is upstream of the pretreatment reactor, or at least upstream of the plug of pretreated lignocellulosic material that is being discharged.

Advantageously, since some of the sulfur dioxide is prevented from being discharged with the pretreated biomass, the sulfur dioxide and/or sulfurous acid loading may be reduced while still maintaining the same concentration of sulfur dioxide and/or sulfurous acid within the pretreatment reactor.

Notably, this is particularly beneficial for pretreatments designed to provide concentrations of sulfur dioxide conventionally corresponding to relatively high equivalent sulfur dioxide loading (e.g., greater than 5%, more particularly greater than about 10%, and even more particularly greater than about 15%). More specifically, the advantages of a relatively high equivalent sulfur dioxide loading (e.g., high pretreatment efficiency) may be realized using a reduced amount of makeup sulfur dioxide and/or sulfurous acid. Accordingly, the costs are reduced.

In one embodiment, the amount of makeup acid fed into the pretreatment reactor is predetermined in dependence upon the amount of sulfur dioxide retained in the headspace, calculated to be retained in the headspace, or estimated to be in the headspace. In one embodiment, the amount of sulfur dioxide retained in the headspace is calculated using the reactor pressure and temperature and headspace volume. Accordingly, a lower sulfur dioxide and/or sulfurous acid loading may be used to provide a higher efficiency pretreatment.

In one embodiment, the equivalent sulfur dioxide loading is selected to provide a predetermined concentration of sulfur dioxide and/or sulfurous acid in the pretreatment reactor during the pretreatment, including the concentration of sulfur dioxide in the headspace.

Figure 2:
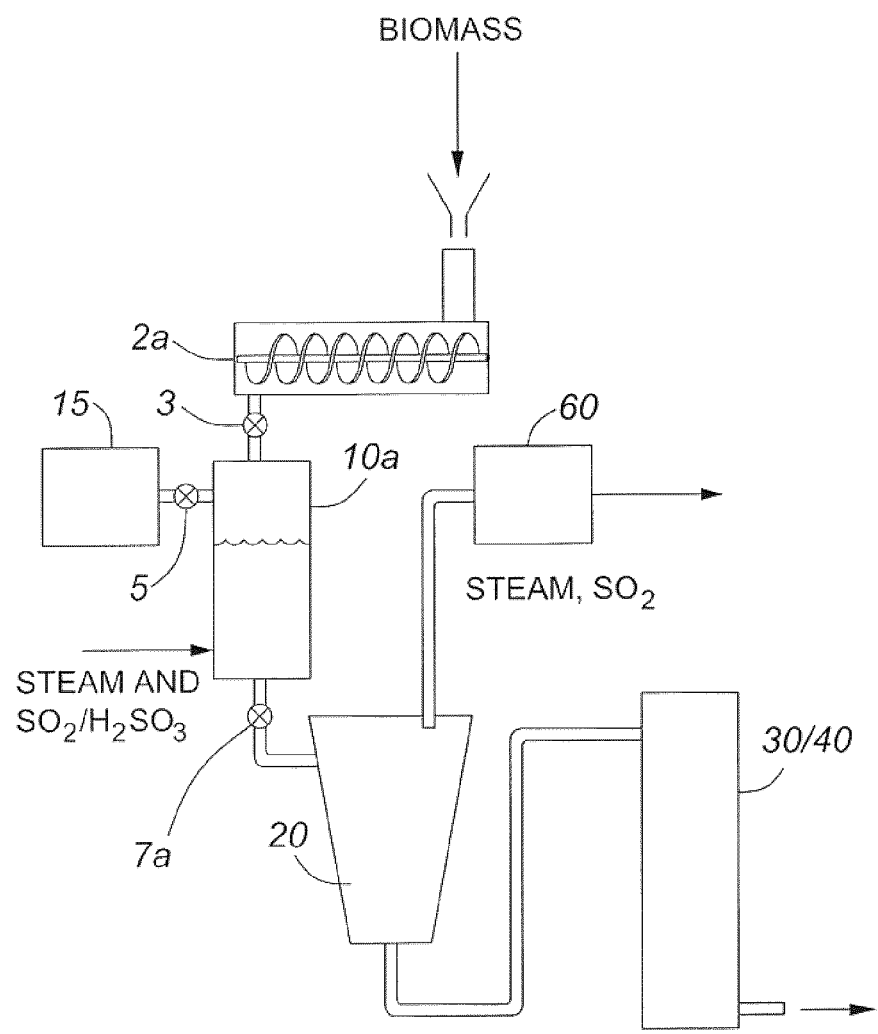
FIG. 2 is a schematic diagram showing a system for hydrolyzing lignocellulosic biomass in accordance with one embodiment of the invention.

Referring to FIG. 2, there is shown a schematic diagram representing an embodiment of a system for hydrolyzing lignocellulosic biomass wherein the pretreatment system includes a batch reactor. In operation, lignocellulosic biomass is fed to a conveyer/dewaterer 2a, which feeds the lignocelluslosic biomass to the pretreatment reactor 10a through open loading valve 3. Optionally, the lignocellulosic biomass is slurried prior to being fed to the conveyor/dewaterer 2a such that the slurried lignocellulosic biomass, which may have a consistency of about 1 wt % to about 12 wt %, and more commonly between about 2 wt % to about 10 wt %, is dewatered to the desired consistency (e.g., greater than about 15 wt %). Alternatively, the lignocellulosic biomass is fed to the conveyor/dewaterer 2a already having a moisture content suitable for pretreatment.

The pretreatment reactor 10a, and/or pretreatment system in general, includes a vapour reservoir 15, the biomass loading valve 3, a reservoir valve 5, and a biomass discharge valve 7a. With the reservoir 5 and discharge 7a valves closed, the pretreatment reactor 10a is filled to a predetermined level (e.g., below the reservoir valve 5), and then the loading valve 3 is closed. Steam, sulfur dioxide, and/or sulfurous acid are fed into the pretreatment reactor 10a, thereby increasing the temperature and/or pressure in the pretreatment reactor 10a. More specifically, sufficient steam is added to bring the lignocellulosic material up to the pretreatment temperature and/or temperature range.

If the reservoir 15 has not been previously charged with sulfur dioxide, the amount of sulfur dioxide and/or sulfurous acid in this system is directly related to the equivalent sulfur dioxide loading. If the vapour reservoir chamber 15 has been previously charged with sulfur dioxide and/or contains sulfur dioxide retained from a previous pretreatment, the amount of sulfur dioxide and/or sulfurous acid in this system may be higher than that provided by equivalent sulfur loading. In general, the steam, sulfur dioxide, and/or sulfurous acid may be injected simultaneously, and/or at different times.

With the reservoir valve 5 open, the lignocellulosic biomass is allowed to reside within the pretreatment reactor 10a for some time (e.g., the residence time). Optionally, additional sulfur dioxide and/or sulfurous acid is added during the pretreatment in order to maintain a constant concentration of sulfur dioxide in the headspace during the pretreatment. Prior to opening the discharge valve 7a, the reservoir valve 5 is closed, thereby trapping a portion of the sulfur dioxide from the headspace in the reservoir 15.

In this embodiment, the discharge valve 7a is opened relatively quickly, thereby providing a rapid pressure release that blows the pretreated lignocellulosic biomass into flash tank 20 and produces a flash stream that is collected at the top of the flash tank 20. More specifically, the pressure difference (i.e., the flash tank 20 is held at a pressure that is lower than the pressure of the heated pretreatment reactor 10a) provides a rapid and "explosive" decompression that may affect the structure of the biomass, and which generally causes the temperature of the pretreated biomass to drop from the pretreatment temperature to a temperature dependent on the pressure in the flash tank 20. For example, if the flash tank is at about atmospheric pressure, the pretreated biomass temperature will be about 100° C. If the flash tank is below atmospheric pressure, the temperature will be lower than 100° C. If the flash tank is held above atmospheric pressure, the temperature will be greater than 100° C. In this embodiment, only one flash tank is illustrated, however, in other embodiments, more than one flash tank is used (e.g., in series).

The cooled, pretreated biomass composition produced by the pretreatment and flashing is fed to enzymatic hydrolysis 30 or a combined hydrolysis/fermentation 30/40, followed by fermentation recovery (not shown). Depending on the temperature and/or pH of the cooled, pretreated biomass composition, it may be conditioned (e.g., subjected to a temperature and/or pH adjustment (not shown)) for hydrolysis.

The flash stream exiting from the top of the flash tank 20 may include steam, gaseous sulfur dioxide, and/or other volatile compounds (e.g., which depend on the pressure of the flash tank). In this embodiment illustrated in FIG. 2, the flash stream is fed to one or more recovery stages 60. In one embodiment, the one or more recovery stages includes a sulfur dioxide recovery. In other embodiments, sulfur dioxide recovery is not necessary and/or not included. In one embodiment, the sulfur dioxide recovery includes a partial condenser (not shown), wherein most of the steam is condensed and collected, and wherein sulfur dioxide gas exits from the top. This sulfur dioxide may be fed to a sulfur dioxide stripping column, or another column that cleans the sulfur dioxide stream for recycling back into the pretreatment.

Advantageously, since a portion of the sulfur dioxide from the headspace is prevented from leaving the pretreatment reactor 10a during the discharge and/or flashing (e.g., since at least a portion of the sulfur dioxide from the headspace is trapped in the vapour reservoir chamber 15 during discharge), less sulfur dioxide may be fed to sulfur dioxide recovery. For example, in one embodiment sufficient sulfur dioxide is retained in the headspace that sulfur dioxide recovery is no longer required, desired, and/or possible. Moreover, since the sulfur dioxide retained in the reservoir 15 may be used in the pretreatment of another batch of lignocellulosic biomass, the amount of makeup sulfur dioxide and/or sulfurous acid that is added to the subsequent batch may be reduced (i.e., relative to a batch that does not use reservoir sulfur dioxide).

For example, in one embodiment, once the pretreated lignocellulosic biomass has been discharged from the pretreatment reactor 10a, the discharge valve 7a is closed, and additional lignocellulosic biomass is fed into the pretreatment reactor 10a. Once the pretreatment reactor 10a has been filled to the predetermined level (e.g., below the reservoir valve 5), the loading valve 3 is closed. Subsequently, steam, sulfur dioxide, and/or sulfurous acid are fed into the pretreatment reactor 10a, thereby increasing the temperature/pressure in the pretreatment reactor 10a. More specifically, sufficient steam is added to bring the lignocellulosic material up to the pretreatment temperature and/or temperature range, while sufficient sulfur dioxide and/or sulfurous acid is added to provide a desired equivalent sulfur dioxide loading (e.g., predetermined to be within a certain range). However, since the reservoir valve 5 is opened prior to or during the initial stages of pretreatment, the amount of makeup steam, sulfur dioxide, and/or sulfurous acid added may be reduced compared to the amount required if reservoir sulfur dioxide was not used (i.e., while still maintaining a relatively large headspace having a relatively high concentration/amount of $SO_2$). For example, in one embodiment, the amount of sulfur dioxide present in the vapour reservoir chamber 15 causes the amount of makeup sulfur dioxide/sulfurous acid required to be significantly less than the initial sulfur dioxide/sulfurous loading.

Figure 3:
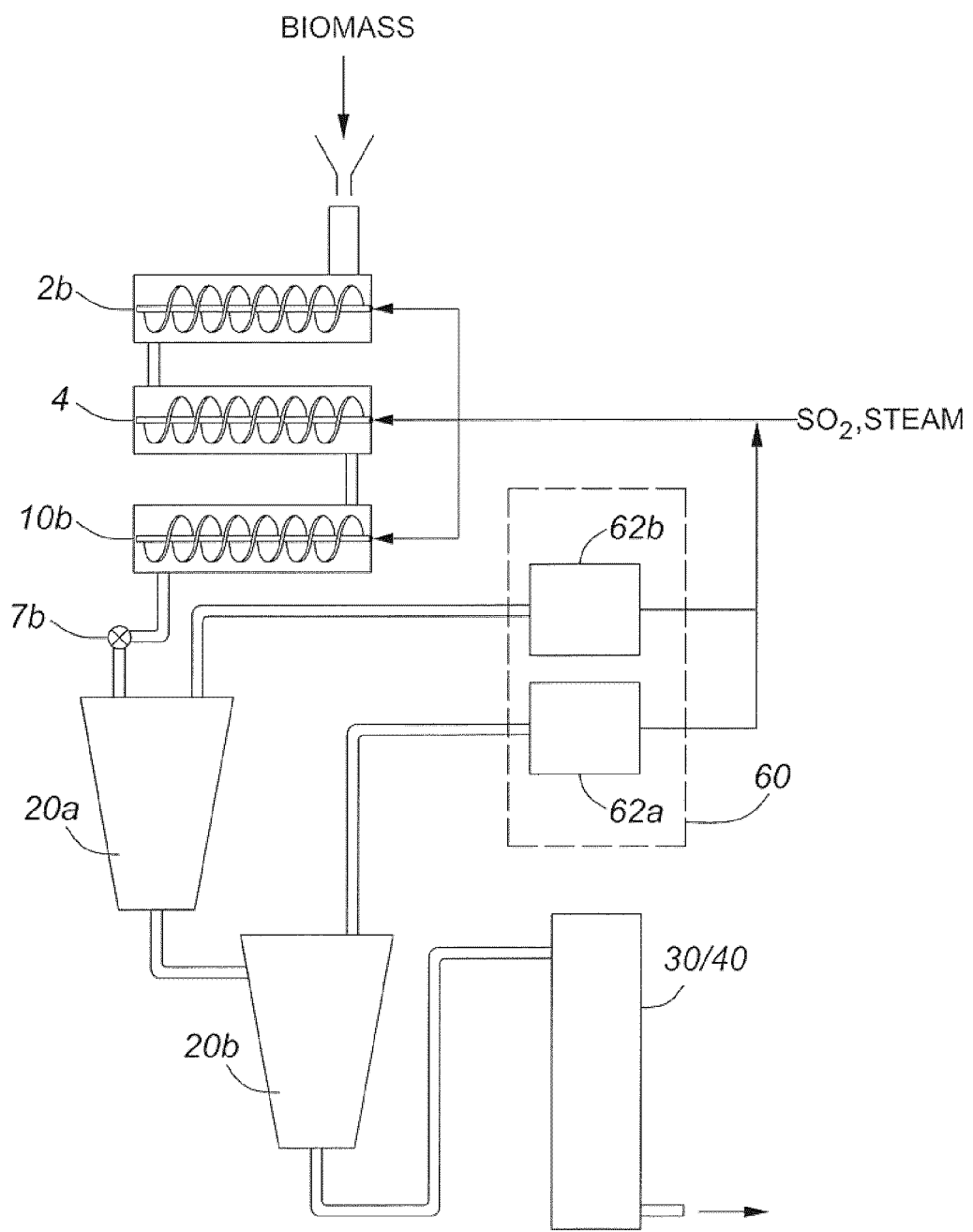
FIG. 3 is a schematic diagram showing a system for hydrolyzing lignocellulosic biomass in accordance with another embodiment of the invention.

Referring to FIG. 3, there is shown a schematic diagram representing an embodiment of a system for pretreating and hydrolyzing lignocellulosic biomass wherein the pretreatment system includes a continuous pretreatment reactor. In operation, lignocellulosic biomass is slurried and provided to a pressurized dewatering system 2b, a heating chamber 4, and a pretreatment reactor 10b. Although illustrated as three separate components for demonstrative purposes, it should be understood that the pretreatment reactor 10b may be part of a pretreatment system that includes these and/or other components, which may be provided as one or more separate but connected components and/or as integrated components.

Optionally, the slurry is soaked prior to being dewatered. The optionally soaked slurry, which may have a consistency of about 1 wt % to about 12 wt %, and more commonly between about 2 wt % to about 10 wt %, is fed to the pressurized dewatering system 2b. The pressurized dewatering system may include a predraining zone (not shown), wherein at least some of the water is removed and fed to a high pressure pump (not shown), which creates a high pressure zone for further dewatering. The pressurized dewatering system 2b reduces the moisture content of the biomass to an amount suitable for pretreatment. For example, in one embodiment, the pressurized dewatering system 2b includes a pressurized dewatering press or a pressurized plug screw feeder (e.g., as described in US Publication No. 2010/0056774). The dewatered biomass (e.g., which may or may not be in plug form and may have a consistency between about 20 wt % and about 67 wt %), may then be fed to the heating chamber 4 and then to the pretreatment reactor 10b. The heating chamber 4 and pretreatment reactor 10b are in fluid communication such that the pressure between the output of the pressurized dewatering system 2b and the discharge valve 7b may be held at a substantially constant value.

The pretreatment reactor 10b, which is a horizontal pretreatment reactor, may include an internal mechanism, such as a screw, auger, conveyor, or similar mechanism, for conveying the lignocellulosic biomass along the length of pretreatment reactor 10b. The residence time may be varied by changing the conveying speed of the internal mechanism (e.g., rotating speed of auger). In general, the lignocellulosic biomass will be fed into the pretreatment reactor 10b at a rate that allows the lignocellulosic biomass to fill the pretreatment reactor 10b such that there is a headspace above the lignocellulosic biomass (e.g., above the incoming biomass and/or at least partially pretreated lignocellulosic biomass composition). In one embodiment, the headspace is greater than about 25% (v/v) of the pretreatment reactor. In one embodiment, the headspace is greater than about 50% (v/v) of the pretreatment reactor. In one embodiment, the headspace is greater than about 75% (v/v) of the pretreatment reactor. In one embodiment, the headspace is greater than about 10%, 20%, 30%, 40%, 60%, 70%, 80%, or 90% (v/v) of the pretreatment reactor.

In general, steam, sulfur dioxide, and/or sulfurous acid may be added in the pressurized dewatering system 2b, in the heating chamber 4, and/or directly into the pretreatment reactor 10b. Accordingly, the pretreatment reactor may be held at a predetermined temperature and/or pressure. For example, in one embodiment, gaseous sulfur dioxide is added to the biomass upstream of the inlet of a pressurized screw press, at the inlet to a pressurized screw press, in a dewatering zone of a pressurized screw press, in the pressurized plug screw feeder, in the heating/impregnation chamber, and/or in the pretreatment reactor. In another embodiment, only the heating chamber 4 and the pretreatment reactor 10b include one or more inlets for injecting steam, sulfur dioxide, and/or sulfurous acid into the pretreatment system. In one embodiment, the sulfur dioxide/ sulfur dioxide is fed into the pretreatment reactor with the biomass. In one embodiment, the pretreatment reactor is charged with sulfur dioxide prior to the biomass being introduced into the pretreatment reactor (e.g., with or without additional sulfur dioxide/sulfurous acid).

In general, the temperature, pressure, and/or residence time of the biomass in the pretreatment reactor may depend upon a number of variables, including the pH in the reaction zone and the desired degree of pretreatment. In one embodiment, the pretreatment temperature is at least 120° C. In one embodiment, the biomass has a residence time in the pretreatment reactor from about 10 seconds to about 20 minutes, or about 10 seconds to about 600 seconds. In one embodiment, the pressure is between about 70 psia and about 800 psia. In one embodiment, the pH is less than about 4, less than about 3, between about 0.5 and about 1.5, or between about 1.0 and about 1.5.

Once the lignocellulosic biomass has been conveyed over the length of the pretreatment reactor (e.g., over a time span corresponding to residence time), the biomass will be substantially pretreated and may be discharged into the flash tank 20a. Since the flash tank 20a is held at a pressure that is lower than the pressure of the pretreatment reactor 10b, the temperature of the pretreated biomass will drop from the pretreatment temperature to a temperature dependent on the pressure in the flash tank 20a. The cooled, pretreated biomass composition produced by the pretreatment and flashing is fed to as second flash tank 20b, followed by enzymatic hydrolysis 30 or a combined hydrolysis/fermentation 30/40, and ethanol recovery (not shown). The second flash tank 20b, is held at a lower pressure than the first flash tank 20a. For example, in one embodiment, the second flash tank 20b is held under vacuum, such that the pretreated biomass is cooled to a temperature compatible with enzymatic hydrolysis. Optionally, the pH of the cooled, pretreated biomass composition is also adjusted to be compatible with enzymatic hydrolysis. The flash stream exiting from the top of the flash tanks 20a/20b may include steam, gaseous sulfur dioxide, and/or other volatile compounds (e.g., which depend on the pressure of the flash tank), and may be fed to one or more recovery stages 60, including, for example, sulfur recovery units 62a and 62b. In one embodiment, sulfur dioxide recovery 60 includes a partial condenser (not shown), wherein most of the steam is condensed and collected, and wherein sulfur dioxide gas exits from the top. This sulfur dioxide may be fed to a sulfur dioxide stripping column, or another column that cleans the sulfur dioxide stream for recycling back into the process.

Advantageously, the continuous pretreatment reactor 10b is configured and/or operated such that the amount of sulfur dioxide in the headspace is maintained while the pretreated lignocellulosic biomass is discharged from valve 7b. Since a large portion of the sulfur dioxide from the headspace is prevented from leaving the pretreatment reactor during the flashing, less sulfur dioxide will be available for the optional sulfur dioxide recovery. If fact, in some embodiments, sufficient sulfur dioxide will be retained in the headspace to eliminate the need and/or desire of sulfur recovery from the flash stream. Moreover, since the sulfur dioxide retained in the headspace may be used in the pretreatment of additional lignocellulosic biomass, the amount of makeup sulfur dioxide and/or sulfurous acid that is continuously and/or intermittently added to maintain sulfur dioxide concentration will be reduced (i.e., relative to a continuous pretreatment that does not maintain a headspace containing sulfur dioxide).

Figure 4:
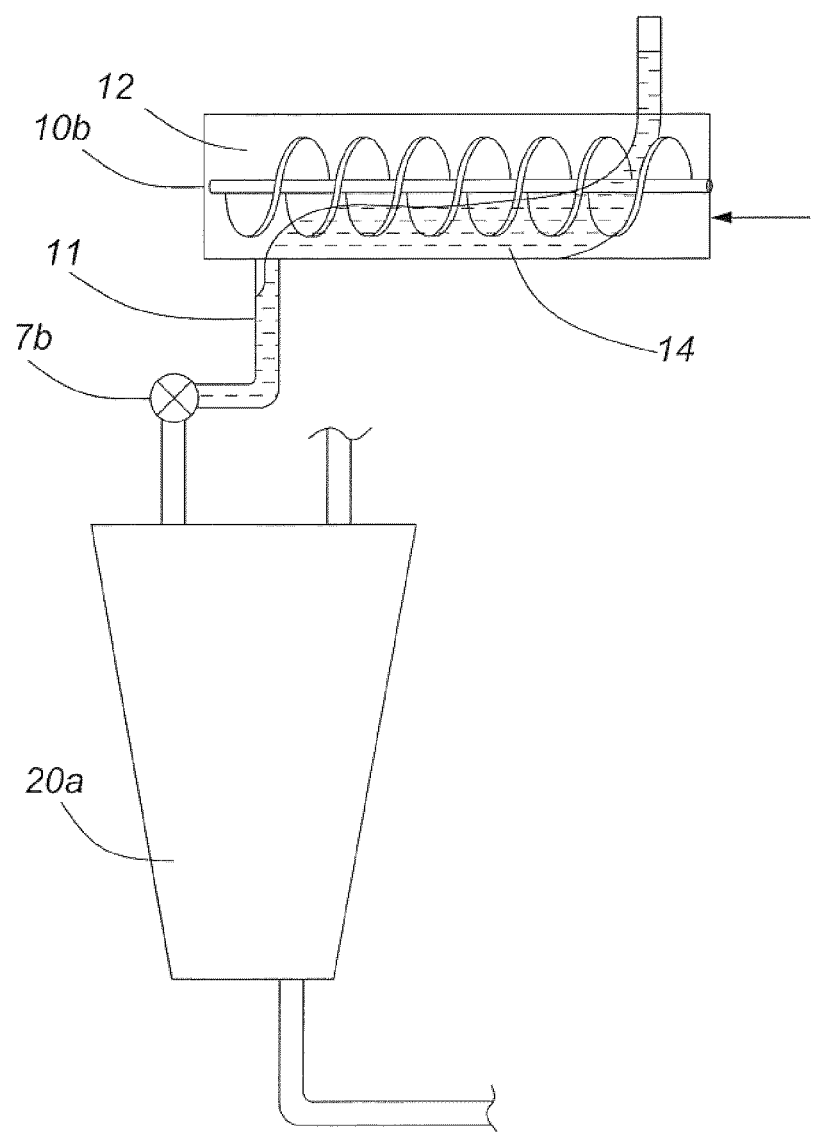
FIG. 4 is a schematic diagram showing part of the pretreatment system illustrated in FIG. 3.

Referring to FIG. 4, there is shown an enlarged view of the continuous pretreatment reactor in FIG. 3. In this embodiment, at least some of the sulfur dioxide in the headspace is retained by providing a liquid seal 11 of pretreated lignocellulosic biomass between the headspace 12 and the discharge valve 7b. For example, as the lignocellulosic biomass, which may be introduced into the pretreatment reactor 10b with a relatively high consistency, propagates along the pretreatment reactor 10b, it absorbs steam and/or is hydrolyzed (e.g., the hemicellulose may be hydrolyzed to provide C5 sugars) to form a slurry of pretreated lignocellulosic biomass. This slurry passes through an opening in the pretreatment reactor 10b into a conduit that is in fluid communication with the discharge valve 7b, thus forming a liquid seal that retains at least some of the sulfur dioxide in the headspace 12. Advantageously, the liquid seal 11 substantially isolates the vapours, such as sulfur dioxide, in the headspace 12, thus preventing them from discharging through discharge valve 7b. In one embodiment, the liquid seal is provided by designing the pretreatment system with a configuration (e.g., length of conduit, conduit shape, conduit diameter, valve aperture, etc.) that reduces the speed of the slurry moving through the conduit and/or by operating the pretreatment system such that the slurry is retained in the conduit (e.g., by selecting the appropriate conveying speed and/or rate of slurry discharge). The pretreated slurry is discharged through valve 7b into the flash tank 20a to provide the pretreated lignocellulosic biomass composition.

Advantageously, the pretreatment system illustrated in FIGS. 3 and 4, uses a horizontal pretreatment reactor. The use of a horizontal pretreatment reactor may be advantageous because there is a larger contact area between the headspace 12 and the slurry 14 (i.e., relative to a vertical reactor). Accordingly, the sulfur dioxide in the headspace will have a larger interface for replacing sulfur dioxide/sulfurous acid consumed during pretreatment, and thus may provide a more uniform acid distribution. In addition, since the liquid seal and headspace are always present, it is less likely that the sulfur dioxide in the headspace will be flashed out (e.g., in contrast to the embodiment in FIG. 2, wherein a small amount may be flashed out). Given the high temperature of pretreatment and the vapour pressure of sulfur dioxide, the amount of sulfur dioxide in the vapour space is expected to be significant during pretreatment. Accordingly, the makeup amount of sulfur dioxide/sulfurous acid that is fed to the pretreatment reactor to provide the required sulfur dioxide concentration may be relatively low. More specifically, the amount of makeup sulfur dioxide required in the system, which is dictated primarily by the amount of sulfur dioxide consumed in the pretreatment and in the liquid phase as the pretreated lignocellulosic material exits the reactor (e.g., as opposed to the amount of sulfur dioxide contained in the gas phase), is substantially minimized. In other words, the embodiments in FIGS. 3 and 4 illustrate a continuous pretreatment system having an isolated headspace that contains a charge of sulfur dioxide, thus lowering overall sulfur dioxide usage and reducing overall operating and capital costs associated with sulfur dioxide makeup and/or recovery.

In one embodiment, the makeup sulfur dioxide and/or sulfurous acid added to the pretreatment reactor 10b is determined using the desired equivalent sulfur dioxide concentration and one or more of the following: operating headspace volume (e.g., related to the fill level), consistency of the lignocellulosic biomass, total pressure of the headspace, partial pressure of sulfur dioxide in the headspace, and/or an estimated amount of sulfur dioxide calculated from the equivalent amount of sulfur dioxide impregnated in the lignocellulosic biomass. Advantageously, the sulfur dioxide in the headspace may be used to drive the reaction, replenish sulfur dioxide in solution, and/or maintain a low pH.

In one embodiment, sulfur dioxide and/or sulfurous acid is added to the pretreatment reactor to provide a predetermined equivalent sulfur dioxide loading and/or predetermined concentration of sulfur dioxide and/or sulfurous acid in the pretreatment reactor. In general, the concentration of sulfur dioxide in the pretreatment reactor will be based on the amount of sulfur dioxide/sulfurous acid in the headspace and the amount of makeup sulfur dioxide/sulfurous acid added (i.e., the loading).

In one embodiment, the amount of sulfur dioxide and/or sulfurous acid in the headspace is determined by monitoring a partial pressure of sulfur dioxide in the headspace. In one embodiment, the partial pressure of sulfur dioxide is monitored indirectly by monitoring the total pressure in the pretreatment reactor and subtracting the steam pressure (e.g., as calculated and/or extrapolated from the pretreatment temperature). In one embodiment, the partial pressure of sulfur dioxide is measured/estimated using a mass flow controller (e.g., mass flow rate of sulfur dioxide into the headspace). In one embodiment, the amount of sulfur dioxide present in the vapour phase is determined using literature sulfur dioxide-water equilibrium data, and using monitored values of temperature and pressure in the reactor. In one embodiment, the partial pressure of sulfur dioxide is determined using an analyzer. In one embodiment, the analyzer is infrared (IR) based. In other embodiment, the analyzer is based on ultraviolet absorption. In another embodiment, the analyzer is based on florescence. In one embodiment, the partial pressure of sulfur dioxide in the headspace is determined by subtracting the steam pressure at the system temperature from the system pressure, while taking the small amount of other volatiles and air pressure into account (e.g., see Example 3).

Enzymatic Hydrolysis

In one embodiment, the pretreated lignocellulosic biomass is conditioned for hydrolysis 30. For example, in one embodiment, the pretreated lignocellulosic biomass composition is cooled and/or pH adjusted. For example, in one embodiment, alkali is added to the pretreated biomass (e.g., to neutralize). Optionally a water content of the pretreated biomass composition is adjusted. After the optional cooling and/or pH adjustment, enzyme(s) may be added to the pretreated biomass using known techniques (e.g., upstream and/or in the hydrolysis reactor). In one non-limiting example, enzyme addition is conducted by adding the enzyme(s) to a reservoir, such as a tank, to form an enzyme solution, which is then introduced to the pretreated biomass composition. In a further non-limiting example, the enzyme(s) is introduced to the pretreated feedstock composition via chemical injection quills, which are commercially available. Alternatively, enzyme may be injected into the pretreated feedstock composition through appropriately sized tubing or via a pipe. In general, addition of enzyme results in an enzymatic hydrolysis wherein the cellulose in the pretreated biomass composition is converted to glucose.

In one embodiment, enzyme addition includes the addition of cellulase, which is an enzyme(s) that breaks cellulose chains into glucose. In particular, the term "cellulase" refers to any of several enzymes produced by fungi, bacteria, or protozoans that catalyze cellulolysis. For example, the term cellulase may denote a multi-enzyme mixture comprising exo-cellobiohydrolases (CBH), endoglucanases (EG) and β-glucosidases (βG) that can be produced by a number of plants and microorganisms. Among the most widely studied, characterized and commercially produced cellulases are those obtained from fungi of the genera *Aspergillus, Humicola, Chrysosporium, Melanocarpus, Myceliopthora, Sporotrichum* and *Trichoderma*, and from the bacteria of the genera *Bacillus* and *Thermobifida*. Cellulase produced by the filamentous fungi *Trichoderma longibrachiatum* comprises at least two cellobiohydrolase enzymes termed CBHI and CBHII and at least four EG enzymes. As well, EGI, EGII, EGIII, EGV and EGVI cellulases have been isolated from *Humicola insolens*. In addition to CBH, EG and βG, there are several accessory enzymes that may aid in the enzymatic digestion of cellulose (see WO 2009/026722 (Scott), which is incorporated herein by reference and Harris et al., 2010, Biochemistry, 49:3305-3316). These include glycoside hydrolase 61 (GH61), swollenin, expansin, lucinen and cellulose-induced protein (Cip). For example, enzymes containing glycoside hydrolase 61 may improve hydrolysis.

In general, the enzyme dose may depend on the activity of the enzyme at the selected pH and temperature, the reaction time, the volume of the reactor, and/or other parameters. It should be appreciated that these parameters may be adjusted as desired by one of skill in the art to achieve optimal conditions. In one embodiment, the cellulase is added at a dosage between about 2 to 20 mg protein per gram cellulase. In one embodiment, the cellulase is added at a dosage between about 2 to 15 mg protein per gram cellulase. In one embodiment, the cellulase is added at a dosage between about 2 to 12 mg protein per gram cellulase. The protein is quantified using either the bicinchoninic acid (BCA) assay or the Bradford assay.

In one embodiment, the hydrolysis is conducted at or near the temperature and/or pH optimum of the enzyme(s). For example, conventional cellulase may have optimum pH values between about 4.5 and about 5.5 and a temperature optimum between about 40° C. and about 60° C. In one embodiment, the enzymatic hydrolysis is conducted at a temperature above about 56° C., or 57° C. Conducting the hydrolysis at temperatures above about 56° C., and in particular, at temperatures above 57° C. or 58° C. may be advantageous in that microbial contamination may be reduced.

In one embodiment, the enzymatic hydrolysis 30 and fermentation 40 are conducted in separate vessels so that each biological reaction can occur at its respective optimal temperature. For example, in one embodiment, the hydrolysis is conducted in one or more dedicated hydrolysis reactors, which may be connected in series or in parallel. In general, the hydrolysis may be conducted in continuous, fed-batch, or batch mode. In one embodiment, the hydrolysis is conducted in continuous mode, which may offer greater productivity and lower costs. For example, in one embodiment, the hydrolysis is conducted one or more continuous stirred tank reactors (CSTRs) and/or one or more plug flow reactors (PFRs). In the plug flow reactor, the slurry is pumped through a pipe or tube such that it exhibits a relatively uniform velocity profile across the diameter of the pipe/tube and such that residence time within the reactor provides the desired conversion. In one embodiment, the hydrolysis includes a plurality of hydrolysis rectors including a PFR and a CSTR in series, as for example, described in U.S. Pat. No. 8,709,770, which is hereby incorporated by reference. In general, the number of hydrolysis reactors in the system may depend on the cost of the reactors, the volume of the pretreated biomass composition, and/or other factors. For a commercial-scale ethanol plant, the typical number of hydrolysis reactors may be, for example, 4 to 12. In order to maintain the desired hydrolysis temperature, the hydrolysis reactors may be jacketed with steam, hot water, or other heat sources. The total residence time in the enzymatic hydrolysis reactors is typically between about 24 hours and about 250 hours, depending on the degree of conversion desired, although could be shorter or longer.

Fermentation

In one embodiment, the hydrolyzed pretreated composition is fed to fermentation 40. In fermentation, the sugars produced during pretreatment (e.g., xylose and glucose) and/or enzymatic hydrolysis (e.g., glucose) are converted to a fermentation product such as an alcohol, and in particular, to ethanol. More specifically, the fermentation uses one or more microorganisms to convert the sugars to the fermentation product.

In general, the fermentation microorganism(s) may include any yeast and/or bacteria. For example, in one embodiment, the fermentation is carried out with *Saccharomyces* spp. yeast, which are attractive because of their capacity to produce ethanol.

In one embodiment, glucose and/or other hexoses derived from the cellulose are fermented to ethanol using a wild-type *Saccharomyces cerevisiae* or a genetically modified yeast. In one embodiment, xylose and or arabinose derived from the hemicelluloses are fermented to ethanol using a yeast strain that naturally contains, or has been engineered to contain, the ability to ferment these sugars to ethanol. Examples of microbes that have been genetically modified to ferment xylose include recombinant *Saccharomyces* strains into which has been inserted either (a) the xylose reductase (XR) and xylitol dehydrogenase (XDH) genes from *Pichia stipitis* (see for example U.S. Pat. Nos. 5,789,210, 5,866,382, 6,582,944 and 7,527,927 and European Patent No. 0450430) or (b) fungal or bacterial xylose isomerase (XI) gene (see for example U.S. Pat. Nos. 6,475,768 and 7,622,284). Examples of yeasts that have been genetically modified to ferment L-arabinose include, but are not limited to, recombinant *Saccharomyces* strains into which genes from either fungal (for example U.S. Pat. No. 7,527,951) or bacterial (for example WO 2008/041840) arabinose metabolic pathways have been inserted. Alternatively, xylose and other pentose sugars may be fermented to xylitol by yeast strains selected from the group consisting of *Candida, Pichia, Pachysolen, Hansenula, Debaryomyces, Kluyveromyces* and *Saccharomyces*.

The dose of the microorganism(s) will depend on other factors, such as the activity of the microorganism, the desired reaction time, the volume of the reactor and other parameters. It should be appreciated that these parameters may be adjusted as desired by one of skill in the art to achieve optimal conditions.

In one embodiment, the fermentation may be performed at or near the temperature and/or pH optimum of the corresponding microorganism. For example, *Saccharomyces cerevisiae* may have optimum pH values between about 4 and about 5.5 and a temperature optimum between about 25° C. and about 35° C.

Regardless of whether the biological conversion includes a separate hydrolysis and fermentation (SHF), simultaneous saccharification and fermentation (SSF), or hybrid hydrolysis and fermentation (HHF) (e.g., wherein the two separate steps are conducted in a same reactor, but at different temperatures), the reactor(s) may contain the C5 sugars and/or the C6 sugars. More specifically, the reactors may contain not only the glucose released during cellulose hydrolysis, but also one or more sugars that may arise from the pretreatment (e.g., xylose, glucose, arabinose, mannose, and/or galactose), for a co-fermentation. Alternatively, in a SHF, the C5 sugars and/or C6 sugars produced during pretreatment are fed to a separate fermentation reactor and/or series of reactors than the C6 sugars produced during enzymatic hydrolysis.

In one embodiment, the fermentation is conducted on a sugar solution containing both C5 and C6 sugars using only *Saccharomyces cerevisiae*. In another embodiment, the fermentation is conducted on a sugar solution containing both C5 and C6 sugars using a mixture wherein C5 utilizing and ethanol producing yeasts (e.g., such as *Pichia fermentans* and *Pichia stipitis*) are cocultured with *Saccharomyces cerevisiae*.

In one embodiment, the fermentation is supplemented with additional nutrients required for the growth of the fermentation microorganism. For example, yeast extract, specific amino acids, phosphate, nitrogen sources, salts, trace elements and vitamins may be added to the hydrolyzate slurry to support their growth. In one embodiment, yeast recycle is employed.

In general, the fermentation may be conducted in continuous, fed-batch, or batch mode. In one embodiment, the fermentation is conducted in continuous mode, which may offer greater productivity and lower costs. In one embodiment, the fermentation is conducted in a plurality of fermentation tanks. For example, in one embodiment, the fermentation is conducted one or more continuous stirred tank reactors (CSTRs) and/or one or more plug flow reactors (PFRs). Advantageously, continuous mode operation may offer less reactor down time and smaller reactor volumes.

Recovery

In general, the fermentation product produced during fermentation may be recovered 50 using methods known in the art. For example, ethanol produced during fermentation may be recovered using a process wherein ethanol is concentrated and/or purified from the fermented solution (e.g., which may or may not have been subjected to a solids-liquid separation to remove unconverted cellulose, insoluble lignin, and/or other undissolved substances).

In one embodiment, ethanol recovery uses one or more distillation columns that separate the ethanol from other components (e.g., water). In general, the distillation column(s) in the distillation unit may be operated in continuous or batch mode, although are typically operated in a continuous mode. Heat for the distillation process may be introduced at one or more points, either by direct steam injection or indirectly via heat exchangers. After distillation, the water remaining in the concentrated ethanol stream (i.e., vapour) may be removed from the ethanol rich vapour by a molecular sieve resin, by membrane extraction, or other methods known to those of skill in the art for concentration of ethanol beyond the 95% that is typically achieved by distillation (e.g., a vapour phase drying). The vapour may then be condensed and denatured.

EXAMPLES

Example 1: Determination of Undissolved Solids Concentration

The determination of the consistency or undissolved solids (UDS) content is carried out as follows. A fixed amount of a sample containing undissolved solids is dispensed into a plastic weigh dish and the weight is recorded accurately using an analytical scale. A glass microfiber filter paper circle of pore size 1.6 microns, appropriately sized for a Buchner funnel, is placed in an aluminum weighing tin and the combined weight of the tin and filter paper is recorded. After transferring the pre-weighed filter paper to the Buchner funnel, the pre-weighed sample is passed through the filter paper to isolate the solids. Small volumes of de-ionized water are used to ensure that the solids are quantitatively transferred from the weigh dish to the Buchner funnel. The solids are then washed using excess deionized water, after which the washed sample and filter paper are transferred into the pre-weighed aluminum tin. Care is taken to ensure the solids are quantitatively transferred. After drying the aluminum tin in a 105° C. oven overnight, the contents are weighed accurately and the UDS is quantified by determining, as a percent, the number of grams of dry solids per gram of sample.

Example 2: Measurement of Dissolved Solids Concentration

The determination of the dissolved solids concentration of a pretreated feedstock composition is carried out as follows. A glass microfiber filter paper circle of pore size 1.6 microns that has not been pre-wetted is placed in a Buchner funnel. A sample of a pretreated feedstock composition is applied to the filter paper and filtered by vacuum. The filtrate is collected and weighed into a pre-weighed aluminum tin. After drying the aluminum tin in a 105° C. oven overnight, the contents are weighed accurately and the dissolved solids are quantified by determining, as a percent, the number of grams of dry solids per gram of filtrate.

The dissolved solids in the pretreated feedstock composition fed to enzymatic hydrolysis and that of the pretreated feedstock composition produced by pretreatment are determined by the foregoing method. A percentage is then calculated from the two values to arrive at a value representing the percent (w/w) of the dissolved solids in the pretreated feedstock composition resulting from pretreating that is fed to the subsequent step of enzymatic hydrolysis.

Example 3: Measurement of Partial Pressure of Sulfur Dioxide in Vapour Space Measurement of the partial pressure of sulfur dioxide in a batch or continuous pretreatment reactor may be carried out as follows. Lignocellulosic biomass, which has been deaerated and then contacted with sulfur dioxide and/or sulfurous acid, is heated to the pretreatment temperature by direct steam injection in a pretreatment reactor. Once the pretreatment reactor indicates that the lignocellulosic biomass has reached the pretreatment temperature (e.g., as measured by a thermocouple), the reactor pressure is measured (e.g., using a pressure gauge). The steam pressure at the pretreatment temperature is retrieved and/or extrapolated from known values (e.g., a steam table), and then subtracted from the reactor pressure to provide the partial pressure of sulfur dioxide. For example, consider the embodiment wherein the pretreatment temperature is 195° C. and the system pressure is measured as 253 psia. According to the steam table, the steam pressure at this temperature (e.g., 195° C.) is 203 psia. The partial pressure of sulfur dioxide in the system is therefore determined to be 50 psia (e.g., 253 psia−203 psia=50 psia). Notably, this determination assumes that the system was deaerated prior to sulfur dioxide addition, and neglects the small partial pressures of other volatile species (e.g., such as acetic acid).

Example 4: Measurement of Amount of Sulfur Dioxide in Headspace

The amount of sulfur dioxide retained in the headspace may be determined using the partial pressure of the sulfur dioxide in the pretreatment system and the volume of the headspace. In particular, the mass, m, of sulfur dioxide in the headspace may be determined by:

$$m = mwPV/RT$$

where mw is the molar mass, P is the partial pressure of sulfur dioxide in the headspace, V is the volume of the headspace, R is the gas constant, and T is the temperature in the headspace.

Given that the molar mass of sulfur dioxide is 64.066 g/mol, the partial pressure of sulfur dioxide in the headspace is 50 psia (i.e., 3.4023 atm) as determined in Example 3, the volume of the headspace is 4 L, R is 0.821 L-atm/mol-K, and the temperature in the headspace is 195° C. (i.e., 468.15 K), the mass of sulfur dioxide in the headspace is given by:

$$m = \frac{(64.066 \text{ g/mol})(3.4023 \text{ atm})(4 \text{ L})}{(0.821 \text{ L-atm/mol-K})(468.15 \text{K})} = 2.3 \text{ g of } SO_2$$

In a batch pretreatment reactor having a vapour reservoir, the volume of the headspace for this calculation is the volume of the vapour reservoir. In a continuous pretreatment reactor, the volume of the headspace may be determined from the total volume of the pretreatment reactor and the slurry level (e.g., which may be measured using a sensor and/or calculated based on the volume/mass of slurry in and out of the pretreatment reactor).

Figure 5:
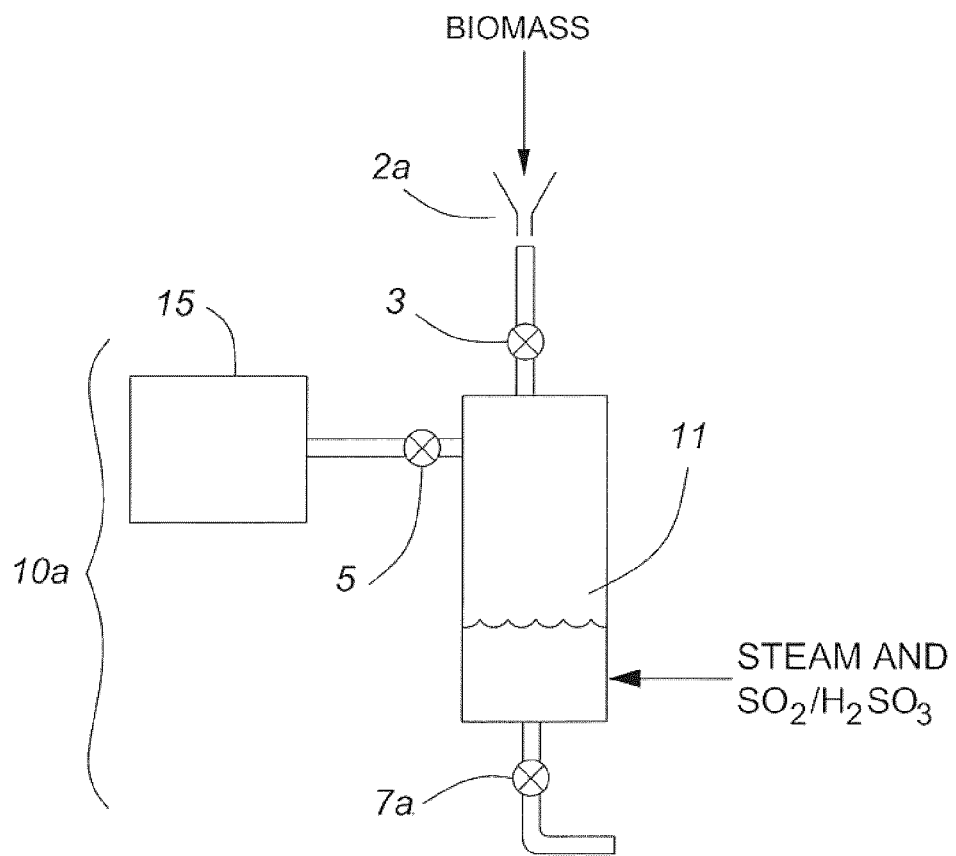
FIG. 5 is a schematic diagram showing a pretreatment reactor in accordance with one embodiment of the instant invention.

For example, consider the batch pretreatment reactor illustrated in FIG. 5. In this embodiment, the pretreatment reactor has a vapour reservoir volume that is approximately 40% of the total pretreatment reactor volume. In particular, the volume of the vapour reservoir 15 is 4 L, while the pretreatment reactor 10*a* has a total volume 10 L (e.g., the vertical chamber 11 has a volume of about 6 L). If the reservoir 15 was sealed near the end of a previous pretreatment when the temperature and pressure of the pretreatment reactor was 195° C. and 253 psia, respectively, then the reservoir should contain about 2.3 g of SO$_2$ (e.g., as illustrated above).

In this embodiment, the pretreatment reactor 10*a* is a steam gun having vapour reservoir 15, and is loaded with the vapour reservoir valve 5 closed. More specifically, pretreatment reactor 10*a* is loaded with 70 g of wheat straw (i.e., equivalent to 60 g of dry lignocellulosic biomass) mixed with about 200 mL of 0.74 M sulfurous acid (i.e., ~6 wt %). The approximate consistency of the sample is 22% (60 g/(70 g+200 g)×100%=22%). Since 200 mL of 0.74 M sulfurous acid contains about 12.2 g of sulfurous acid, which is equivalent to about 9.6 g of sulfur dioxide, the equivalent sulfur loading is approximately 16 wt % (e.g., 9.6 g/60 g*100%=16 wt %). In this embodiment, the amount of sulfur dioxide in the vapour reservoir (e.g., 2.3 g) is almost a quarter of that available as a result of the sulfur dioxide loading (e.g., 9.6 g). Accordingly, it is clear that the extra 2.3 g of sulfur dioxide that is present in the vapour reservoir may significantly improve and/or drive the pretreatment with the same equivalent sulfur dioxide loading (e.g., 16 wt %), or alternatively, may allow less sulfur dioxide/sulfurous acid to be loaded into the pretreatment reactor.

Alternatively, consider the continuous pretreatment reactor illustrated in FIG. 4. In this embodiment, the pretreatment reactor 10a is fed a pressurized wheat straw slurry prepared by soaking the wheat straw followed by dewatering, wherein the dewatering provides a slurry having a consistency of about 22%. This pressurized slurry is fed into the pretreatment reactor such that a headspace having a volume that is approximately 40% of the total pretreatment volume is present. Gaseous sulfur dioxide is fed into the pretreatment system (e.g., near or upstream the biomass inlet of the pretreatment reactor) at a rate that provides a sulfur dioxide loading of 16 wt %. However, since some of the sulfur dioxide is retained within the headspace (e.g., about 2.3 g as discussed above), the amount of sulfur dioxide available for pretreatment may be higher than that provided solely by the steady state sulfur dioxide loading. Accordingly, the steady state sulfur dioxide loading may be reduced in dependence upon a volume of the headspace. Although the 60% filled 10 L pretreatment reactor will include more wheat straw than that exemplified above (e.g., with regard to the batch reactor), the 2.3 g of retained sulfur dioxide will still be significant because it is a continuous system.

Of course, the above embodiments have been provided as examples only. It will be appreciated by those of ordinary skill in the art that various modifications, alternate configurations, and/or equivalents will be employed without departing from the spirit and scope of the invention. For example, in the above-described embodiments the pretreatment is acid-catalyzed pretreatment using sulfur dioxide and/or sulfurous acid. However, in other embodiments, the pretreatment is an acid-catalyzed pretreatment using hydrogen chloride (HCl) gas or carbon dioxide ($CO_2$). In yet another embodiment, the pretreatment is a base-catalyzed pretreatment that uses ammonia ($NH_3$) gas. In addition, in the above-described embodiments the vapour reservoir is disposed on a side of the pretreatment reactor. In other embodiments, the vapour reservoir is disposed on top of the pretreatment reactor. Accordingly, the scope of the invention is therefore intended to be limited solely by the scope of the appended claims.

The invention claimed is:

1. A process for hydrolyzing lignocellulosic biomass comprising:
   a) feeding lignocellulosic biomass and acid into a pretreatment reactor, said acid comprising at least one of sulfur dioxide and sulfurous acid;
   b) heating said lignocellulosic biomass in the pretreatment reactor for a time and at a temperature sufficient to provide a slurry comprising pretreated lignocellulosic biomass, said slurry adjacent a headspace comprising sulfur dioxide;
   c) removing said slurry from the pretreatment reactor;
   d) preventing at least a portion of the sulfur dioxide in the headspace from exiting the pretreatment reactor as the slurry is removed;
   e) hydrolyzing cellulose in the removed slurry in the presence of cellulase to produce glucose; and
   f) contacting additional lignocellulosic biomass with the sulfur dioxide prevented from exiting the pretreatment reactor in step d) under conditions selected to pretreat the additional lignocellulosic biomass.

2. The process according to claim 1, wherein an amount of acid fed into the pretreatment reactor in step a) is determined in dependence upon an amount of sulfur dioxide retained in the headspace.

3. The process according to claim 1, comprising monitoring a partial pressure of sulfur dioxide in the headspace.

4. The process according to claim 3, wherein adding acid in step a) comprises injecting sulfur dioxide into the pretreatment reactor at a rate selected in dependence upon the monitored partial pressure.

5. The process according to claim 1, wherein the pretreatment reactor is a batch pretreatment reactor, wherein the sulfur dioxide is retained within a vapour reservoir chamber, and wherein step d) comprises:
   closing a valve to the vapour reservoir chamber to trap a portion of the sulfur dioxide therein; and
   discharging the slurry from the pretreatment reactor with the valve closed.

6. The process according to claim 1, wherein the pretreatment reactor is a continuous mode pretreatment reactor, and wherein step d) comprises maintaining a liquid seal between the headspace and a discharge of the pretreatment reactor, said liquid seal comprising the slurry.

7. The process according to claim 1, wherein the amount of acid fed into the pretreatment reactor in step a) is selected to provide an equivalent sulfur dioxide loading that is at least 1% weight sulfur dioxide on weight of dry lignocellulosic biomass.

8. The process according to claim 1, wherein feeding lignocellulosic biomass and acid into a pretreatment reactor comprises feeding acid impregnated lignocellulosic biomass into the pretreatment reactor.

9. The process according to claim 1, wherein the time is between about 1 minute and about 30 minutes.

10. The process according to claim 1, wherein the temperature is between about 170° C. and about 240° C.

11. The process according to claim 1, wherein a volume of the headspace is greater than about 20% of a volume of the pretreatment reactor.

12. The process according to claim 1, wherein a volume of the headspace is greater than about 50% of a volume of the pretreatment reactor.

13. The process according to claim 1, wherein a volume of the headspace is greater than about 70% of a volume of the pretreatment reactor.

14. The process according to claim 1, wherein the lignocellulosic biomass has a consistency at an inlet of the pretreatment reactor that is greater than about 15 wt %.

15. The process according to claim 1, wherein heating said lignocellulosic biomass in step b) comprises injecting steam into the pretreatment reactor.

16. The process according to claim 15, wherein feeding acid into the pretreatment reactor in step a) comprises injecting sulfur dioxide into the pretreatment reactor.

17. The process according to claim 16, wherein the sulfur dioxide is injected with the steam.

18. A process for pretreating lignocellulosic biomass comprising:
   a) feeding acid and lignocellulosic biomass into a pretreatment reactor, said acid comprising at least one of sulfur dioxide and sulfurous acid, said acid added to the pretreatment reactor with the lignocellulosic biomass, separate from the lignocellulosic biomass, or a combination thereof;
   b) adding heat to the pretreatment reactor such that said lignocellulosic biomass and acid are heated for a time and at a temperature sufficient to provide a slurry comprising pretreated lignocellulosic biomass, said slurry disposed within the pretreatment reactor adjacent a headspace, said headspace comprising sulfur dioxide;
   c) removing the slurry from the pretreatment reactor;
   d) reserving at least a portion of the sulfur dioxide in the headspace within at least one of the pretreatment reactor and a reservoir connected to the pretreatment reactor as the slurry is removed from the pretreatment reactor; and e) pretreating additional lignocellulosic biomass in the presence of the reserved sulfur dioxide.

19. The process according to claim 18, wherein the pretreatment reactor is a batch pretreatment reactor, and wherein step d) comprises sealing sulfur dioxide within the reservoir as the slurry is being removed.

20. The process according to claim 18, wherein the pretreatment reactor is a continuous pretreatment reactor, and wherein step d) comprises maintaining a liquid seal between the headspace and a slurry discharge valve.

21. A process for hydrolyzing lignocellulosic biomass comprising:
   a) feeding lignocellulosic biomass and acid into a pretreatment reactor, said acid comprising at least one of sulfur dioxide and sulfurous acid;
   b) heating said lignocellulosic biomass in the pretreatment reactor for a time and at a temperature sufficient to provide a slurry comprising pretreated lignocellulosic biomass, said slurry adjacent a headspace comprising sulfur dioxide;
   c) removing at least a portion of said slurry from the pretreatment reactor;
   d) preventing at least a portion of the sulfur dioxide in the headspace from exiting the pretreatment reactor as the at least a portion of the slurry is removed such that a concentration of sulfur dioxide in at least a region of the headspace of the pretreatment reactor is substantially maintained while the slurry is removed;
   e) hydrolyzing cellulose in the removed slurry in the presence of cellulase to produce glucose; and
   f) selecting an amount of make-up sulfur dioxide to be added to the pretreatment reactor in dependence upon an amount of sulfur dioxide prevented from exiting the pretreatment reactor.

* * * * *